US012077789B2

(12) United States Patent
Golynskiy et al.

(10) Patent No.: US 12,077,789 B2
(45) Date of Patent: *Sep. 3, 2024

(54) POLYMERASES, COMPOSITIONS, AND METHODS OF USE

(71) Applicant: ILLUMINA, INC., San Diego, CA (US)

(72) Inventors: Misha Golynskiy, San Diego, CA (US); Mariko Matsuura, San Diego, CA (US); Saurabh Nirantar, Singapore (SG); Hamed Tabatabaei Ghomi, Cambridge (GB); Seth McDonald, San Diego, CA (US); Ryan Craig, San Diego, CA (US); Sergio Peisajovich, San Diego, CA (US); Kyrie Johnson, San Diego, CA (US); Kay Klausing, San Diego, CA (US); Eric Murtfeldt, San Diego, CA (US); Alexandra Exner, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/829,866

(22) Filed: Jun. 1, 2022

(65) Prior Publication Data

US 2023/0047225 A1 Feb. 16, 2023

Related U.S. Application Data

(60) Provisional application No. 63/233,243, filed on Aug. 14, 2021.

(51) Int. Cl.
C12N 9/12 (2006.01)
C12Q 1/6874 (2018.01)

(52) U.S. Cl.
CPC ......... C12N 9/1252 (2013.01); C12Q 1/6874 (2013.01); C12Y 207/07007 (2013.01)

(58) Field of Classification Search
None
See application file for complete search history.

(56) References Cited

U.S. PATENT DOCUMENTS

| | | | |
|---|---|---|---|
| 5,882,904 A | 3/1999 | Riedl et al. | |
| 5,948,666 A | 9/1999 | Callen et al. | |
| 6,333,183 B1 | 12/2001 | Evans et al. | |
| 6,492,161 B1 | 12/2002 | Hjorleifsdottir et al. | |
| 7,892,797 B2 | 2/2011 | Mitsis et al. | |
| 8,268,605 B2 | 9/2012 | Sorge et al. | |
| 8,283,149 B2 | 10/2012 | Niu et al. | |
| 8,460,910 B2 | 6/2013 | Smith et al. | |
| 8,623,628 B2 | 1/2014 | Ost et al. | |
| 8,852,910 B2 | 10/2014 | Smith et al. | |
| 9,273,352 B2 | 3/2016 | Smith et al. | |
| 9,447,389 B2 | 9/2016 | Smith et al. | |
| 9,447,445 B2 | 9/2016 | Hsieh et al. | |
| 9,677,057 B2 | 6/2017 | Bomati et al. | |
| 9,765,309 B2 | 9/2017 | Chen et al. | |
| 10,017,750 B2 | 7/2018 | Smith et al. | |
| 10,059,928 B2 | 8/2018 | Smith et al. | |
| 10,150,954 B2 | 12/2018 | Bomati et al. | |
| 10,421,996 B2 | 9/2019 | Bomati et al. | |
| 10,526,648 B2 | 1/2020 | Cressina et al. | |
| 10,696,955 B2 | 6/2020 | Bomati et al. | |
| 10,745,751 B2 | 8/2020 | Bomati et al. | |
| 10,870,836 B2 | 12/2020 | Chen et al. | |
| 11,001,816 B2* | 5/2021 | Klausing | C12Y 207/07007 |
| 11,104,888 B2 | 8/2021 | Golynskiy et al. | |
| 11,136,564 B2 | 10/2021 | Smith et al. | |
| 11,198,854 B2 | 12/2021 | Bomati et al. | |
| 11,473,067 B2 | 10/2022 | Smith et al. | |
| 11,560,552 B2 | 1/2023 | Golynskiy et al. | |
| 11,634,697 B2* | 4/2023 | Klausing | C12Y 207/07007 435/194 |
| 2002/0132249 A1 | 9/2002 | Patel et al. | |
| 2003/0228616 A1 | 12/2003 | Arezi et al. | |
| 2005/0069908 A1 | 3/2005 | Sorge et al. | |
| 2006/0240439 A1 | 10/2006 | Smith et al. | |
| 2006/0281109 A1 | 12/2006 | Barr Ost et al. | |
| 2007/0048748 A1 | 3/2007 | Williams et al. | |
| 2009/0170167 A1 | 7/2009 | Mitsis et al. | |
| 2011/0269211 A1 | 11/2011 | Bourn et al. | |
| 2011/0301041 A1 | 12/2011 | Davidson et al. | |
| 2012/0020537 A1 | 1/2012 | Garcia et al. | |
| 2012/0094296 A1 | 4/2012 | Tabata et al. | |
| 2014/0296082 A1 | 10/2014 | Gardner | |

(Continued)

FOREIGN PATENT DOCUMENTS

| AU | 2007201277 A1 | 4/2007 |
|---|---|---|
| CA | 2581471 A1 | 4/2006 |

(Continued)

OTHER PUBLICATIONS

Bornscheuer et al. Curr Protoc Protein Sci. Nov. 2011;Chapter 26:Unit26.7 (Year: 2011).*
Yoshikuni et al. Curr Opin Chem Biol. Apr. 2007;11(2):233-9 (Year: 2007).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Accession Q56366. Dec. 15, 1998 (Year: 1998).*
Accession BHV94537. Aug. 6, 2020. (Year: 2020).*
Kranaster et al., "Engineered DNA Polymerases in Biotechnology," Chembiochem, Oct. 2010, vol. 11, No. 15, pp. 2077-2084.
Laos et al., "DNA polymerases engineered by directed evolution to incorporate non-standard nucleotides," Frontiers in Microbiology, Oct. 2014, vol. 5, No. 565, 14 pages.

(Continued)

Primary Examiner — Christian L Fronda
(74) Attorney, Agent, or Firm — Mueting Raasch Group

(57) ABSTRACT

Presented herein are altered polymerase enzymes for improved incorporation of nucleotides and nucleotide analogues, in particular altered polymerases that maintain low pre-phasing rates when using ambiently stored polymerases, as well as methods and kits using the same.

33 Claims, 7 Drawing Sheets

Specification includes a Sequence Listing.

(56) References Cited

U.S. PATENT DOCUMENTS

| | | |
|---|---|---|
| 2015/0024463 A1 | 1/2015 | Smith et al. |
| 2015/0376582 A1 | 12/2015 | Chen et al. |
| 2016/0002721 A1 | 1/2016 | Liu et al. |
| 2016/0032377 A1 | 2/2016 | Chen et al. |
| 2016/0090579 A1 | 3/2016 | Bomati et al. |
| 2016/0115461 A1 | 4/2016 | Smith et al. |
| 2017/0275602 A1 | 9/2017 | Smith et al. |
| 2017/0355970 A1 | 12/2017 | Chen et al. |
| 2018/0119115 A1 | 5/2018 | Lin Wu et al. |
| 2018/0298358 A1 | 10/2018 | Smith et al. |
| 2019/0330602 A1 | 10/2019 | Wang et al. |
| 2020/0002689 A1 | 1/2020 | Olejnik et al. |
| 2020/0056230 A1 | 2/2020 | Bomati et al. |
| 2020/0080065 A1 | 3/2020 | Fuller et al. |
| 2020/0087637 A1 | 3/2020 | Iyidogan |
| 2020/0087638 A1 | 3/2020 | Iyidogan |
| 2020/0117968 A1 | 4/2020 | Ulyate |
| 2020/0131484 A1 | 4/2020 | Golynskiy et al. |
| 2020/0181587 A1* | 6/2020 | Klausing ........ C12Y 207/07007 |
| 2020/0231947 A1 | 7/2020 | Peist et al. |
| 2021/0147927 A1 | 5/2021 | Bomati et al. |
| 2021/0324353 A1 | 10/2021 | Zhai et al. |
| 2021/0348141 A1 | 11/2021 | Klausing et al. |
| 2022/0056424 A1 | 2/2022 | Golynskiy et al. |

FOREIGN PATENT DOCUMENTS

| | | |
|---|---|---|
| CN | 101180390 A | 5/2008 |
| EP | 0701000 A3 | 3/1996 |
| EP | 0822256 A2 | 2/1998 |
| EP | 0892058 A2 | 1/1999 |
| EP | 0701000 B1 | 1/2001 |
| EP | 1208230 B1 | 11/2005 |
| EP | 2325304 A1 | 5/2011 |
| EP | 1664287 B1 | 11/2011 |
| WO | 9106678 A1 | 5/1991 |
| WO | 9739150 A1 | 10/1997 |
| WO | 0123411 A2 | 4/2001 |
| WO | 0132887 A1 | 5/2001 |
| WO | 0210358 A2 | 2/2002 |
| WO | 02101358 A2 | 12/2002 |
| WO | 03048387 A2 | 6/2003 |
| WO | 03054139 A2 | 7/2003 |
| WO | 2004018497 A2 | 3/2004 |
| WO | 2004039947 A2 | 5/2004 |
| WO | 2005024010 A1 | 3/2005 |
| WO | 2006037064 A2 | 4/2006 |
| WO | 2006120433 A1 | 11/2006 |
| WO | 2007076057 A2 | 7/2007 |
| WO | 2007123744 A2 | 11/2007 |
| WO | 2008029084 A1 | 3/2008 |
| WO | 2008029085 A2 | 3/2008 |
| WO | 2008051530 A2 | 5/2008 |
| WO | 2008083393 A2 | 7/2008 |
| WO | 2009131919 A2 | 10/2009 |
| WO | 2011026194 A1 | 3/2011 |
| WO | 2011135280 A2 | 11/2011 |
| WO | 2012058096 A1 | 5/2012 |
| WO | 2012154934 A1 | 11/2012 |
| WO | 2014139596 A1 | 9/2014 |
| WO | 2014142921 A1 | 9/2014 |
| WO | 2015200693 A1 | 12/2015 |
| WO | 2016033315 A2 | 3/2016 |
| WO | 2016054096 A1 | 4/2016 |
| WO | 2017042040 A1 | 3/2017 |
| WO | 2018126470 A1 | 7/2018 |
| WO | 2018148723 A1 | 8/2018 |
| WO | 2018148724 A1 | 8/2018 |
| WO | 2018148726 A1 | 8/2018 |
| WO | 2018148727 A1 | 8/2018 |
| WO | 2020048329 A1 | 3/2020 |
| WO | 2020056044 A1 | 3/2020 |
| WO | 2020060811 A1 | 3/2020 |
| WO | 2020092830 A1 | 5/2020 |
| WO | 2020117968 A2 | 6/2020 |
| WO | 2020136170 A2 | 7/2020 |

OTHER PUBLICATIONS

Lee et al., Database Accession # F4HMC2, integrated into UniProtKB/TrEMBL, Jun. 28, 2011, 2 pages.

Li et al., "Structure-based design of Taq DNA polymerases with improved properties of dideoxynucleotide incorporation," PNAS USA, Aug. 1999, vol. 96, pp. 9491-9496.

Liu et al., "Identification of Conserved Residues Contributing to the Activities of Adenovirus DNA Polymerase," Journal of Virology, Dec. 2000, vol. 74, No. 24, pp. 11681-11689.

Loakes et al., "Evolving a Polymerase for Hydrophobic Base Analogues," Journal of the American Chemical Society, Oct. 2009, vol. 131, No. 41, pp. 14827-14837.

Lutz et al., "Recognition of a Non-standard Base Pair by thermostable DNA Polymerases," Bioorganic & Medicinal Chemistry Letters, Jun. 1998, vol. 8, No. 10, pp. 1149-1152.

Metzker et al., "Termination of DNA synthesis by novel 3'-modified-deoxyribonucleoside 5'-triphosphates," Nucleic Acids Research, Oct. 1994, vol. 22, No. 20, pp. 4259-4267.

Minnick et al., "A thumb subdomain mutant of the large fragment of *Escherichia coli* DNA polymerase I with reduced DNA binding affinity, processivity, and frameshift fidelity," The Journal of Biological Chemistry, Oct. 1996, vol. 271, No. 40, pp. 24954-24961.

Morrison et al., "Combinatorial alanine-scanning," Current Opinion in Chemical Biology, Jun. 2001, vol. 5, No. 3, pp. 302-307.

Ngo et al., "Computational Complexity, Protein Structure Prediction, and the Levinthal Paradox," in the Protein Folding Problem and Tertiary Structure Prediction, Merz et al (ed.). Birkhauser, Boston, MA; 1994, pp. 433 and 492-495.

Oksman et al., "Conformation of 3'-Substituted 2',3'-Dideoxyribonucleosides in Aqueous Solution; Nucleoside Analogues with Potential Antiviral Activity," Nucloesides & Nucleotides, 1991, vol. 10, No. 1-3, pp. 567-568.

Oksman et al., "Solution Conformations and Hydrolytic Stability of 2'- and 3'-Substituted 2',3'-Dideoxyribonucleosides, Including Some Potential Inhibitors of Human Immunodeficiency Virus," Journal of Physical Organic Chemistry, Nov. 1992, vol. 5, pp. 741-747.

Patel et al., "DNA polymerase active site is highly mutable: Evolutionary consequences," PNAS USA, May 2000, vol. 97, No. 10, pp. 5095-5100.

Patel et al., "Prokaryotic DNA Polymerase I: Evolution, Structure, and "Base Flipping" Mechanism for Nucleotide Selection," Journal of Molecular Biology, May 2001, vol. 308, pp. 823-837.

Pavlov et al., "In Vivo consequences of putative active site mutations in yeast DNA polymerase alpha, epsilon, delta, and zeta," Genetics, Sep. 2001, vol. 159, No. 1, pp. 47-64.

Pavlov et al., "Recent developments in the optimization of thermostable DNA polymerases for efficient applications," Trends in Biotechnology, May 2004, vol. 22, No. 5, pp. 253-260.

Polesky et al., "Identification of Residues Critical for the Polymerase Activity of the Klenow Fragment of DNA Polymerase I from *Escherichia coli*," Journal of Biological Chemistry, Aug. 1990, vol. 265, No. 24, pp. 14579-14591.

Querellou et al., Database Accession # Q9HH06, integrated into UniProtKB/TrEMBL Feb. 20, 2007; 1 page.

Rodriguez et al., "Crystal structure of a pol α family DNA polymerase from the hyperthermophilic archaeon *Thermococcus* sp. 9°N-7," Journal of Molecular Biology, Jun. 2000, vol. 299, No. 2, pp. 447-462.

Sadowski et al., "The sequence-structure relationship and protein function prediction," Current Opinion in Structural Biology, Jun. 2009, vol. 19, No. 3, pp. 357-362.

Seffernick et al., "Melamine deaminase and Atrazine chlorohydrolase: 98 percent identical but functionally different," Journal of Bacteriology, Apr. 2001, vol. 183, No. 8, pp. 2405-2410.

Sen et al., "Developments in directed evolution for improving enzyme functions," Applied Biochemistry and Biotechnology, Dec. 2007, vol. 143, pp. 212-223.

(56) References Cited

OTHER PUBLICATIONS

Sensen et al., "Probable DNA-directed DNA Polymerase," PIR accession No. S75407, 1997, 2 pages.
Shinkai et al., "The Conserved Active Site Motif A of *Escherichia coli* DNA Polymerase 1 is Highly Mutable," Journal of Biological Chemistry, Jun. 2001, vol. 276, No. 22, pp. 18836-18842.
Shinkai et al., "In Vivo Mutagenesis by *Escherichia coli* DNA Polymerase I," Journal of Biological Chemistry, Dec. 2001, vol. 276, No. 50, pp. 46759-46764.
Song et al., "An Amino Acid Residue in the Middle of the Fingers Subdomain is Involved in neq DNA Polymerase Processivity: Enhanced Processivity of Engineered Neq DNA Polymerase and its PCR Application," Protein Engineering Design and Selection, Nov. 2010, vol. 23, No. 11, pp. 835-842.
Southworth et al., "Cloning of thermostable DNA polymerases from hyperthermophilic marine Archaea with emphasis on *Thermococcus* sp. 9 degrees N-7 and mutations affecting 3'-5' Exonuclease activity," PNAS USA, May 1996, vol. 93, No. 11, pp. 5281-5285.
St. Clair et al., "3'-Azido-3"-Deoxythymidine Triphosphate as an Inhibitor and Substrate of Purified Human Immunodeficiency Virus Reverse Transcriptase," Antimicrobial Agents and Chemotherapy, Dec. 1987, vol. 31, No. 12, pp. 1972-1977.
Stachelhaus et al., "The specificity-conferring code of adenylation domains in nonribosomal peptide synthetases," Chemistry and Biology, Aug. 1999, vol. 6, No. 8, pp. 493-505.
Steitz, "DNA Polymerases: Structural Diversity and Common Mechanisms," Journal of Biological Chemistry, Jun. 1999, vol. 274, No. 25, pp. 17395-17398.
Suzuki et al., "Low Fidelity Mutants in the O-Helix of Thermus aquaticus DNA Polymerase I," The Journal of Biological Chemistry, Apr. 1997, vol. 272, No. 17, pp. 11228-11235.
Suzuki et al., "Random mutagenesis of Thermus aquaticus DNA polymerase I: Concordance of immutable sites in vivo with the crystal structure," PNAS USA, Sep. 1996, vol. 93, No. 18, pp. 9670-9675.
Tomic-Canic et al., "A Simple Method for Site-Specific Mutagenesis that Leaves the Rest of the Template Unaltered," Methods in Molecular Biology, 1996, vol. 57, pp. 259-267.
Truniger et al., "Function of the C-terminus of φ29 DNA polymerase in DNA and terminal protein binding," Nucleic Acids Research, Jan. 2004, vol. 32, No. 1, pp. 361-370.
Tunitskaya et al., "Structural-functional Analysis of Bacteriophage T7 RNA Polymerase," Biochemistry (Moscow), Oct. 2002, vol. 67, No. 10, pp. 1124-1135.
UniProt [Online] Database; XP002775656, UniProt: Q52415; Nov. 1, 1996, 1 page.
Uniprot—Acension—https://www.uniprot.org/uniprot/Ps75/P61875.txt?version+65, printed Aug. 31, 2018, 4 pages.
Vanhercke et al., "Reducing mutational bias in random protein libraries," Analytical Biochemistry, Dec. 2005, vol. 339, pp. 9-14.
Wang et al., "Human DNA polymerase alpha: predicted functional domains and relationships with viral DNA polymerases," FASEB Journal, Jan. 1989, vol. 3, pp. 14-21.
Welch et al., "Syntheses of Nucleosides Designed for Combinatorial DNA Sequencing," Chemistry: European Journal, Mar. 1999, vol. 5, No. 3, pp. 951-960.
Whisstock et al., "Prediction of protein function from protein sequence," Quarterly Reviews of Biophysics, Aug. 2003, vol. 36, No. 3, pp. 307-340.
Witkowski et al., "Conversion of β-Ketoacyl synthase to a Malonyl Decarboxylase by replacement of the active cysteine with glutamine," Biochemistry, Aug. 1999, vol. 38, pp. 11643-11650.
Yang et al., "A conserved Tyr residue is required for sugar selectivity in a Pol alpha DNA polymerase," Biochemistry, Aug. 2002, vol. 41, pp. 32, pp. 10256-10261.
Yang et al., "Steady-State Kinetic Characterization of RB69 DNA Polymerase Mutants That Affect dNTP Incorporation," Biochemistry, Jun. 1999, vol. 38, No. 25, pp. 8094-8101.
Zavgorodny et al., "1-Alkylthioalkylation of Nucleoside Hydroxyl Functions and Its Synthetic Applications: A New Versatile Method in Nucleoside Chemistry," Tetrahedron Letters, Dec. 1991, vol. 32, No. 51, pp. 7593-7596.
Zavgorodny et al., "S,X-acetals in nucleoside chemistry. III. Synthesis of 2'- and 3'-O-azidomethyl derivatives of ribonucleosides," Nucleosides, Nucleotides & Nucleic Acids, 2000, vol. 19, No. 10-12, pp. 1977-1991.
Alignments, Result 1 US-15-688-473-95, U.S. Appl. No. 15/632,733 Sequence 95; Result 2 US-15-632-733-25, U.S. Appl. No. 15/632,733 Sequence 25; 4 pages.
Arezi et al., "Efficient and High Fidelity Incorporation of Dye-terminators by a Novel Archaeal DNA Polymerase Mutant," Journal of Molecular Biology, Sep. 2002, vol. 322, No. 4, pp. 719-729.
Banerjee et al., "Improving enzymes for biomass conversion: A basic research perspective," Bioenergy Research, Jan. 2010, vol. 3, pp. 82-92.
Bebenek et al., "The Effects of dNTP Pool Imbalances on Frameshift Fidelity during DNA Replication," The Journal of Biological Chemistry, Feb. 1992, vol. 267, No. 6, pp. 3589-3596.
Beckman et al., "On the Fidelity of DNA Replication: Manganese Mutagenesis in Vitro," Biochemistry, Oct. 1985, vol. 24, No. 21, pp. 5810-5817.
Blasco et al., "Characterization and Mapping of the Pyrophosphorolytic Activity of the Phage ø29 DNA Polymerase," The Journal of Biological Chemistry, Apr. 1991, vol. 266, No. 12, pp. 7904-7909.
Bonnin et al., "A Single Tyrosine Prevents Insertion of Ribonucleotides in the Eukaryotic-type φ29 DNA Polymerase," Journal of Molecular Biology, Jul. 1999, vol. 290, No. 1, pp. 241-251.
Branden et al., "Chapter 16: Prediction, Engineering, and Design of Protein Structures," in Introduction to Protein Structure. Branden and Tooze (Ed.) Garland Publishing Inc.: New York; 1991. Cover page, publisher's page, and p. 247.
Brautigam et al., "Structural and functional insights provided by crystal structures of DNA polymerases and their substrate complexes," Current Opinion in Structural Biology, Feb. 1998, vol. 8, pp. 54-63.
Broun et al., "Catalytic plasticity of fatty acid modification enzymes underlying chemical diversity of plant lipids," Science, Nov. 1998, vol. 282, pp. 1315-1317.
Canard et al., "DNA polymerase fluorescent substrates with reversible 3'-tags," Gene, Oct. 1994, vol. 148, No. 1, pp. 1-6.
Chen, "DNA polymerases drive DNA sequencing by-synthesis technologies: both past and present," Frontiers in Microbiology, Jun. 2014, vol. 5, 12 pages.
Chica et al., "Semi-rational approaches to engineering enzyme activity: combining the benefits of directed evolution and rational design," Current Opinions in Biotechnology, Aug. 2005, vol. 16, No. 4, pp. 378-384.
Cooper et al., "Chapter 2: The Composition of Cells," in the Cell: A Molecular Approach, Fourth Edition. ASM Press (Ed). Sinauer Associates, Inc.: Sunderland, MA; 2007. Cover page, publisher's page, and pp. 52-53.
Database UniProt [Online], "DNA Polymerase," Methanotorris formicicus Mc-S-70, retrieved from EBI accession No. UNIPORT:H1KYG9, Mar. 1, 2001. Database accession No., https://pir3.uniprot.org/uniprot/H1KYG9.txt. [retrieved Oct. 27, 2020] 2 pages.
Database UniProt [Online], "DNA Polymerase," Thermococcus hydrothermalis, retrieved from EBI accession No. UNIPORT:Q0HH05, Mar. 21, 2012. Database accession No., https://pir3.uniprot.org/uniprot/Q9HH05.txt. [retrieved Oct. 27, 2020] 3 pages.
Database UniProt [Online], "DNA Polymerase," UniProtKB/Swiss-Prot: Q7SIG7.1, accession No. Q7SIG7, created Feb. 20, 2007, sequence updated Dec. 15, 2003, annotation updated Sep. 29, 2021, 9 pages.
Database UniProt [Online], RecName: Full=DNA polymerase {EC0:00002561 RuleBase:RU000442}; EC=2.7.7.7 {EC0:00002561 RuleBase:RU000442}; XP002746835, retrieved from EBI accession No. UNIPORT:A8AACO Database accession No. A8AACO; sequence, Oct. 23, 2007, 2 pages.
Database UniProt [Online], "RecName: Full=DNA polymerase; EC=2.7.7.7; AltName:Full=Pwo polymerase; EGKVITRGLE

(56) References Cited

OTHER PUBLICATIONS

IVRRDWSEIA KETQARVLET ILKHGDVEEA VRIVEVIQK LANYEIPPEK", XP002746834, retrieved from EBI accession No. UNIPORT:P61876, Database accession No. P61876, Jun. 7, 2004, 2 pages.
Devos et al., "Practical limits of functional prediction," Proteins: Structure, Function and Genetics, Oct. 2000, vol. 41, pp. 98-107.
DNA polymerase, Wikipedia, Jun. 6, 2019, 16 pages.
Dong et al., "Mutational studies of human DNA polymerase α: Identification of residues critical for deoxynucleotide binding and misinsertion fidelity of DNA synthesis," The Journal of Biological Chemistry, Nov. 1993, vol. 268, No. 32, pp. 24163-24174.
Dong et al., "Mutational Studies of human DNA Polymerase α: Serine 867 in the second most conserved region among α-like DNA polymerases is involved in primer binding and mispair primer extension," The Journal of Biological Chemistry, Nov. 1993, vol. 268, No. 32, pp. 24175-24182.
Doublie et al., "Crystal structure of a bacteriophage T7 DNA replication complex at 2.2 Å resolution," Nature, Jan. 1998, vol. 391, pp. 251-258.
Evans et al., "Improving dideoxynucleotide-triphosphate utilisation by the hyper-thermophilic DNA polymerase from the archaeon Pyrococcus furiosus," Nucleic Acids Research, Mar. 2000, vol. 28, No. 5, pp. 1059-1066.
Franklin et al., "Structure of the Replicating Complex of a Pol α Family DNA Polymerase," Cell, Jun. 2001, vol. 105, No. 5, pp. 657-667.
Gardner et al., "Acyclic and dideoxy terminator preferences denote divergent sugar recognition by archaeon and Taq DNA polymerases," Nucleic Acids Research, Jan. 2002, vol. 30, No. 2, pp. 605-613.
Gardner et al., "Comparative kinetics of nucleotide analog incorporation by vent DNA polymerase," The Journal of Biological Chemistry, Mar. 2004, vol. 279, No. 12, pp. 11834-11842.
Gardner et al., "Determinants of nucleotide sugar recognition in an archaeon DNA polymerase," Nucleic Acids Research, Jun. 1999, vol. 27, No. 12, pp. 2545-2553.
Gardner et al., "DNA Polymerases in Biotechnology," Frontiers in Microbiology, Dec. 2014, vol. 5, No. 659, 3 pages.
Gardner et al., "Rapid Incorporation Kinetics and Improved Fidelity of a Novel Class of 3'-OH Unblocked Reversible Terminators," Nucleic Acids Research, May 2012, vol. 40, No. 15, pp. 7404-7415.
Genbank Accession Number: National Center for Biotechnology Information, National Library of Medicine, National Institutes of Health, Accession No. EHP87084.1, "DNA polymerase Pol2 [Methanotorris formicicus Mc-S-70]," Bethesda, MD, Jan. 23, 2012, 3 pages.
Genbank Accession Number: National Center for Biotechnology Information, National Library of Medicine, National Institutes of Health, Accession No. Q7S1G7.1, "RecName: Full=DNA polymerase; AltName: Full=D Tok Pol," Bethesda, MD, Sep. 9, 2012, 5 pages.

GenBank Accession Number: National Center for Biotechnology Information, National Library of Medicine, National Institutes of Health, GenBank Locus AIF05993, Accession No. AIF05993.1, "putative DNA-directed DNA polymerase type II (DPA, polB1) [uncultured marine group II/III euryarchaeote KM3_18_D06]". Bethesda, MD, Jul. 15, 2014, 3 pages.
GenBank: National Center for Biotechnology Information, National Library of Medicine, National Institutes of Health, GenBank Locus EHR76801, Accession No. EHR76801.1, "DNA polymerase elongation subunit (family B) [uncultured Candidatus Poseidoniales archaeon]". Bethesda, MD, Mar. 18, 2015, 2 pages.
Glick et al., "In Vitro Production and Screening of DNA Polymerase η Mutants for Catalytic Diversity," BioTechniques, Nov. 2002, vol. 33, No. 5, pp. 1136-1144.
Griffiths, et al., "New High Fidelity Polymerases from *Thermococcus* Species," Protein Expression and Purification, Jan. 2007, vol. 52, No. 1, pp. 19-30.
Guo et al., "Protein tolerance to random amino acid change," PNAS, Jun. 2004, vol. 101, No. 25, pp. 9205-9210.
Hashimoto et al., "Crystal Structure of DNA Polymerase from Hypertheramophilic Archaeon Pyrococcus kodakaraensis KOD1," Journal of Molecular Biology, Feb. 2001, vol. 306, pp. 469-477.
Hopfner et al., "Crystal structure of a thermostable type B DNA polymerase from Thermococcus gorgonarius," PNAS USA, Mar. 1999, vol. 96, pp. 3600-3605.
International Preliminary Report on Patentability for PCT/US2019/064524, mailed Jun. 17, 2021, 11 pages.
International Search Report and Written Opinion in PCT/EP2022/065121, mailed Oct. 13, 2022, 13 pages.
International Search Report and Written Opinion in PCT/US2019/059246, mailed Mar. 30, 2020, 27 pages.
International Search Report and Written Opinion in PCT/US2019/064524, mailed Jul. 10, 2020, 16 pages.
Joyce, "Choosing the right sugar: How polymerases select a nucleotide substrate," PNAS, Mar. 1997, vol. 94, pp. 1619-1622.
Joyce et al., "Function and Structure Relationships in DNA Polymerases," Annual Review Biochemistry, Jul. 1994, vol. 63 pp. 777-822.
Joyce et al., "Polymerase Structures and Function: Variations on a Theme?" Journal of Bacteriology, Nov. 1995, vol. 177, No. 22, pp. 6321-6329.
Joyce et al., "Techniques used to study the DNA polymerase reaction pathway," Biochimica et Biophysica Acta (BBA)—Proteins & Proteomics, May 2010, vol. 1804, No. 5, pp. 1032-1040.
Kaushik et al., "Significant of the 0-helix residues of *Escherichia coli* DNA polymerase I in DNA synthesis: dynamics of the dNTP binding pocket," Biochemistry, Jun. 1996, vol. 35, No. 22, pp. 7256-7266.
Kim et al., Database Accession #E9KLD9, integrated into UniProtKB/TrEMBL, Apr. 5, 2011, 2 pages.

\* cited by examiner

FIG. 1

```
SEQ ID NO:1  MILDTDYITENGKPVIRVFKKENGEFKIEYDRTFEPYFYALLKDDSAIEDVKKVTAKRHG   60
SEQ ID NO:2  MILTDYITKDGKPIIRIFKKENGEFKIELDPHFQPYIYALLKDDSAIEEIKAIKGERHG   60
SEQ ID NO:7  MILDADYITEDGKPVIRVFKKEKGEFKINYDRDFEPYIYALLKDDSAIEDIKKITAERHG   60
SEQ ID NO:5  MILDTDYITEDGKPVIRIFKKENGEFKIEYDRTFEPYFYALLKDDSAIEEVKKITAERHG   60
SEQ ID NO:4  MILDVDYITEEGKPVIRLFKKENGKFKIEHDRTFRPYIYALLRDDSKIEEVKKITGERHG   60
SEQ ID NO:3  MILDADYITEDGKPIIRIFKKENGEFKVEYDRNFRPYIYALLKDDSQIDEVRKITAERHG   60
SEQ ID NO:6  MILDADYITEDGKPIIRIFKKERGEFKVEYDRTFRPIYALLKDDSAIDEVKKITAERHG   60
              **  **** ** * * * * **** *** *  *  * ****** ** **  *   ***

SEQ ID NO:1  TVVKVRAEKVQKKFLGRPIEVWKLYFNHPQDVPAIRDRIRAHPAVVDIYEYDIPFAKRY  120
SEQ ID NO:2  KTVRVLDAVKVRKFLGREVEVWKLIFEHPQDVPAMRGKIREHPAVVDIYEYDIPFAKRY  120
SEQ ID NO:7  TTVRVTRAERVKKKFLGRPVEVWKLYFTHPQDVPAIRDKIREHPAVVDIYEYDIPFEAKRY 120
SEQ ID NO:5  TVVTVKRVERVQKKFLGRPVEVWKLYFTHPQDVPAIRDKIREHPAVIDIYEYDIPFAKRY  120
SEQ ID NO:4  KIVRIVDVEKVRKKFLGKPITVWKLYLEHPQDVPTIREKVREHPAVVDIFEYDIPFAKRY  120
SEQ ID NO:3  KIVRIIDAEKVRKKFLGRPIEVWKLIFEHPQDVPAIRDKIREHSAVIDIFEYDIPFAKRY  120
SEQ ID NO:6  KIVRITEVEKVQKKFLGRPIEVWKLYLEHPQDVPAIREKIREHPAVVDIFEYDIPFAKRY  120
              * * *   *  **** *  *** *   *****    * **   * ** ******

SEQ ID NO:1  LIDKGLIPMEGDEELTMLAFDIETLYHEGEEFGTGPILMISYADGSEARVITWKKIDLPY 180
SEQ ID NO:2  LIDKGLIPMEGDEELKLLAFAIATFYHEGDEEFGKGEIIMISYADEEEARVITWKNIDLPY 180
SEQ ID NO:7  LIDKGLIPMEGNEELRMLAFDIETLYHEGEEFGEGPILMISYADEEGARVITWKNIDLPY 180
SEQ ID NO:5  LIDKGLVPMEGDEELKMLAFAIATLYHEGEEFAEGPILMISYADEEGARVITWKNVDLPY 180
SEQ ID NO:4  LIDKGLIPMEGEEELKILAFDIETLYHEGEEFGKGPIIMISYADENEAKVITWKNIDLPY 180
SEQ ID NO:3  LIDKGLIPMEGDEELKLLAFAIAFAIATLYHEGEEFAKGPIIMISYADEEEAKVITWKKIDLPY 180
SEQ ID NO:6  LIDKGLTPMEGNEELTFLAVAIATLYHEGEEFGKGPIIMISYADEEGAKVITWKSIDLPY 180
              ****** **** ***   *      ****** ** ** *****     * ***  ****
```

FIG. 1 cont'd

```
SEQ ID NO:1  VDVVSTEKEMIKRFLRVVREKDPDVLITYNGDNEFDFAYLKKRCEELGIKFTLGRDG--SE  238
SEQ ID NO:2  VDVVSNEREMIKRFVQVVKEKDPDVIITYNGDNFDLPYLIKRAEKLGVRLIVLGRDKEHPE 240
SEQ ID NO:7  VESVSTEKEMIKRFLKVIQEKDPDVLITYNGDNEFDFAYLKKRSETLGVKFTLGRDG--SE  238
SEQ ID NO:5  VDVVSTEREMIKRFLRVVKEKDFDVLITYNGDNEFDFAYLKKRCEKLGINFALGRDG--SE  238
SEQ ID NO:4  VEVVSSEREMIKRFLRIIREKDPDIIVTYNGDSFDFPYLAKRAEKLGIKLTIGRDG--SE   238
SEQ ID NO:3  VEVVSSEREMIKRFLKVIREKDFDVIITYNGDSFDLPYLVKRAEKLGIKIPLGRDG--SE   238
SEQ ID NO:6  VEVVSSEREMIKRLVKVIREKDPDVIITYNGDNEFDFPYLLKRAEKLGIKLPLGRDN--SE  238
             * *:.*:*:*** ** :::*:** ::::****.:* * ** *::**: * :   *

SEQ ID NO:1  PKIQRMGDRFAVEVKGRIHFDLYPVIRRTINLPTYTLEAVYEAVFGKPKEKVYAEEIAQA   298
SEQ ID NO:2  PKIQRMGDSFAVEIKGRIHFDLFPVVRRTINLPTYTLEAVYEAVLGKTKSKLGAEEIAAI  300
SEQ ID NO:7  PKIQRMGDRFAVEVKGRIHFDLYPVIRRTINLPTYTLEAVYEAVFGQPKEKVYAEEIAQA  298
SEQ ID NO:5  PKIQRMGDRFAVEVKGRIHFDLYPVIRRTINLPTYTLETVYEAIFGEAVYEAVFGQPKEKVYAEEITTA  298
SEQ ID NO:4  PKMQRIGDMTAVEVKGRIHFDLYHVIRRTINLPTYTLEAVYEAIFGKPKEKVYADEIAKA  298
SEQ ID NO:3  PKMQRLGDMTAVEIKGRIHFDLYHVIRRTINLPTYTLEAVYEAIFGKEAIFGKEVYAHEIAEA  298
SEQ ID NO:6  PKMQRMGDSLAVEIKGRIHFDLFPVIRRTINLPTYTLEAVYEAIFGKSKEKVYAHEIAEA  298
             **:**:** :***:*******: *:*********:::*::

SEQ ID NO:1  WESGEGLERVARYSMEDAKVTYELGREFFPMEAQLSRLIGQSIWDVSRSSTGNLVEWFLL  358
SEQ ID NO:2  WETEESMKKLAQYSMEDARATYELGKEFFPMEAELAKLIGQSVWDVSRSSTGNLVEWYLL  360
SEQ ID NO:7  WESGEGLERVARYSMEDAKATYELGKEFFPMEAQLSRLIGQSLWDVSRSSTGNLVEWFLL  358
SEQ ID NO:5  WETGENLERVARYSMEDAKATYELGKEFFPMEAQLSRLIGQSLWDVSRSSTGNLVEWFLL  358
SEQ ID NO:4  WESGENLERVAKYSMEDAKATYELGKEFLPMEIQLSRLVGQPLWDVSRSSTGNLVEWFLL  358
SEQ ID NO:3  WETGKGLERVAKYSMEDAKVTYELGREFFPMEAQLSRLVGQPIWDVSRSSTGNLVEWYLL  358
SEQ ID NO:6  WETGKGLERVAKYSMEDAKVTFELGKEFFPMEAQLARLVGQPVWDVSRSSTGNLVEWFLL  358
             **: : :::: *******: *:***:** ***: *::*:*: ***************:**
```

FIG. 1 cont'd

```
SEQ ID NO: 1  RKAYKRNELAPNKPDERELARR-RGGYAGGYVKEPERGLWDNIVYLDFRSLYPSIIITHN   417
SEQ ID NO: 2  RVAYARNELAPNKPDEEEYKRRLRTTYLGGYVKEPEKGLWENITYLDFRSLYPSIIVTHN   420
SEQ ID NO: 7  RKAYERNELAPNKPDERELARR-AESYAGGYVKEPEKGLWENIVYLDYKSLYPSIIITHN   417
SEQ ID NO: 5  RKAYERNELAPNKPDERELARR-RQSYEGGYVKEPERGLWENIVYLDFRSLYPSIIITHN   417
SEQ ID NO: 4  RKAYERNEVAPNKPSEEEYQRRLRESYTGGFVKEPEKGLWENIVYLDFRALYPSIIITHN   418
SEQ ID NO: 3  RKAYERNELAPNKPDEREYERRLRESYAGGYVKEPEKGLWEGIVSLDFRSLYPSIIITHN   418
SEQ ID NO: 6  RKAYERNELAPNKPDEREYERRLRESYEGGYVKEPEKGLWEGIVSLDFRSLYPSIIITHN   418
              * **:**** **** ** *:::* *  *****:***: :*:**: ***:******:***

SEQ ID NO: 1  VSPDTLNREGCKEYDVAPEVGHKFECKDFPGFIPSLLGDLLEERQKIKRKMKATVDPLEKK  477
SEQ ID NO: 2  VSPDTLEKEGCKNYDVAPIVGYMGYPKARWYSKECAESVTAWGRHYIEMTIREIEEKFGEKVL  480
SEQ ID NO: 7  VSPDTLNREGCREYDVAPQVGHRFECKDFPGFIPSILGDLLEERQKVKKMKATVDPIERK  477
SEQ ID NO: 5  VSPDTLNREGCKEYDVAPQVGHRFECKDFPGFIPSLLGDLLEERQKIKKKMKATIDPIERK  477
SEQ ID NO: 4  VSPDTLNLEGCKNYDIAPQVGHRFECKDIPGFIPSLGHLLEERQKIKTRMKETQDPIEKI  478
SEQ ID NO: 3  VSPDTLNREGCREYDVAPEVGHKFECKDFPGFIPSLLKRLLDERQEIKRKMKASKDPIEKK  478
SEQ ID NO: 6  VSPDTLNRENCKEYDVAPQVGHRFECKDFPGFIPSLLGNLLEERQKIKKRMKESKDPVEKK  478
              ****** : * : ** **::****:******* ::  ** :: . **  ::**

SEQ ID NO: 1  LLDYRQRAIKILANSFYGYYGYAKARWYCKECAESVTAWGREYIEMVIRELEEKFGEKVL  537
SEQ ID NO: 2  MLDYRQRAIKLLANSYYGMGYPKARWYSKECAESVTAWGRHYIEMTIREIEEKFGEKVL  540
SEQ ID NO: 7  LLDYRQRAIKILANSYYGYYGYANARWYCRECAESVTAWGRQYIETTMREIEEKFGEKVI  537
SEQ ID NO: 5  LLDYRQRAIKILANSFYGYYGYARARWYCKECAESVTAWGREYITTMTIKEIEEKYGFKVI  537
SEQ ID NO: 4  LLDYRQRAIKILANSYYGYYGYAKARWYCKECAESVTAWGRKYIELVWKELEEKFGEKVL  538
SEQ ID NO: 3  MLDYRQRAIKILANSYYGYYGYAKARWYCKECAESVTAWGREYIEFVRKELEEKFGEKVL  538
SEQ ID NO: 6  LLDYRQRAIKILANSYYGYYGYAKARWYCKECAESVTAWGRQYIDLVRRELES-RGFKVL  537
              :***:*****:***.:**:**: ******.:*********: *: :.:::** . * *:
```

FIG. 1 cont'd

```
SEQ ID NO:1   YADTDGLHATIPGADAETVKKKAKEFLKYINPKLPGLLELEYEGFYVRGFFVTKKKYAVI    597
SEQ ID NO:2   YADTDGFYATIPGEKPELIKKKAKEFLNYINSKLPGLLELEYEGFYLRGFFVTKKRYAVI    600
SEQ ID NO:7   YADTDGFFATIPGADAETVKKKTKEFLNYINPRLPGLLELEYEGFYRRGFFVTKKKYAVI    597
SEQ ID NO:5   YSDTDGFFATIPGADAETVKKKAMEFLKYINAKLPGALELEYEGFYKRGFFVTKKKYAVI    597
SEQ ID NO:4   YIDTDGLYATIPGGESEEIKKKALEFVKYINSKLPGLLELEYEGFYKRGFFVTKKRYAVI    598
SEQ ID NO:3   YIDTDGLYATIPGAKPEEIKKKALEFVDYINAKLPGLLELEYEGFYVRGFFVTKKKYALI    598
SEQ ID NO:6   YIDTDGLYATIPGAKHEEIKEKALKFVEYINSKLPGLLELEYEGFYARGFFVTKKKYALI    597
              * ****:: ****   ** :*:***:** :*: ** :*******:*:**:************ .

SEQ ID NO:1   DEEGKITTRGLEIVRRDWSEIAKETQARVLEAILKHGDVEEAVRIVKEVTEKLSKYEVPP    657
SEQ ID NO:2   DEEGKRITTRGLEIVRRDWSEIAKETQAKVLEAILKHGDVEEAVRIVKEVTEKLSKYEVPL    660
SEQ ID NO:7   DEEDKITTRGLEIVRRDWSEIAKETQARVLEAILKHGDVEEAVRIVKEVTEKIAKYRVPL    657
SEQ ID NO:5   DEEGKITTRGLEIVRRDWSEIAKETQARVLEAILKHGDVEEAVRIVKEVTEKLSRYEVPP    657
SEQ ID NO:4   DEEGKVTTRGLEIVRRDWSEIAKETQARVLETILKHGDVEEAVRIVKEVIQKLANYEIPF    658
SEQ ID NO:3   DEEGKIITTRGLEIVRRDWSEIAKETQAKVLEAILKHGNVEEAVKIVKEVTEKLSKYEIPP    658
SEQ ID NO:6   DEEGKIVTRGLEIVRRDWSEIAKETQAKVLEAILKHGNVDEAVKIVKEVTEKLSKYEIPF    657
              ***.:  ***********************:**:******* ::**:****** ::* .

SEQ ID NO:1   EKLVIHEQITRDLRDYKATGPHVAVAKRLAAARGVKIRPGTVISYIVLKGSGRIGDRAIPA    717
SEQ ID NO:2   EKLVIHEQITRDLKDYKAIGPHVAIAKRLAARGIKVKPGTIISYIVLKGSGKISDRVILL    720
SEQ ID NO:7   EKLVIYEQITRNLRDYRATGPHVAVAKRLAARGIKIRPGTVISYIVSYIVLKGPGRVGDRAIPF    717
SEQ ID NO:5   EKLVIHEQITRDLKDYKATGPHVAVAKRLAARGVKIRPGTVISYIVSYIVLKGSGRIGDRAIPF    717
SEQ ID NO:4   EKLAIYEQITRPLHEYKAIGPHVAVAKRLAAKGVKLAAKGVKVRPGMVIGYIVLRGDGPISNRAILA    718
SEQ ID NO:3   EKLVIYEQITRPLHEYKAIGPHVAVAKRLAARGVKLAARGVKVRPGMVIGYIVLRGDGPISKRAILA    718
SEQ ID NO:6   EKLVIYEQITRPLSEYKAIGPHVAVAKRLAAKGVKVKPGMVIGYIVLRGDGPISKRAIAI    717
              *** * ****.* * *::*******:** ::*::.:* *.:.*****:*. :...*
```

FIG. 1 cont'd

```
SEQ ID NO: 1  DEFDPTKHRYDAEYYIENQVLPAVERILKAFGYRKEDLRYQKTKQVGLGAWLKVKGKK-    775
SEQ ID NO: 2  TEYDPRKHKYDPDYYIENQVLPAVLRILEAFGYRKEDLRYQSSKQTGLDAWLKR----    774
SEQ ID NO: 7  DEFDPAKHRYDAEYYIENQVLPAVLRILEAFGYRKEDLRYQKTKQAGLGAWLKPKTGS-   775
SEQ ID NO: 5  DEFDPTKHKYDAEYYIENQVLPAVERILRAFGYRKEDLRYQKTRQVGLSAWLKPKGT-    774
SEQ ID NO: 4  EEYDPKKHKYDAEYYIENQVLPAVLRILEGFGYRKEDLRYQKTRQVGLTSWLNIKKS--   775
SEQ ID NO: 3  EEFDLRKHKYDAEYYIENQVLPAVLRILEAFGYRKEDLRWQKTKQTGLTAWLNIKKKGS   777
SEQ ID NO: 6  EEFDPKKHKYDAEYYIENQVLPAVLRILRAFGYRKEDLKYQKTKQVGLGAWLKFGS---   773
              *.*. **.:*.******.*******:**..****.*****.*** :.:..* :.:**   :***:
```

POLYMERASES, COMPOSITIONS, AND METHODS OF USE

RELATED APPLICATIONS

This application claims priority to Provisional Application No. 63/233,243 filed Aug. 14, 2021 entitled Polymerases, Compositions, and Methods of Use, the contents of which is incorporated herein in its entirety.

SEQUENCE LISTING

This application contains a Sequence Listing electronically submitted via EFS-Web to the United States Patent and Trademark Office as an ASCII text file entitled "2022-06-01-SeqListing_ST25.txt" having a size of 158 kilobytes and created on 13 Aug. 2021. The information contained in the Sequence Listing is incorporated by reference herein.

FIELD

The present disclosure relates to, among other things, altered polymerases for use in performing a nucleotide incorporation reaction, particularly in the context of nucleic acid sequencing by synthesis.

BACKGROUND

Sequencing by synthesis (SBS) typically requires the controlled (i.e., one at a time) incorporation of the correct complementary nucleotide opposite the nucleic acid being sequenced. This allows for accurate sequencing by adding nucleotides in multiple cycles as each nucleotide residue is sequenced one at a time, thus preventing an uncontrolled series of incorporations from occurring. The incorporated nucleotide is read using an appropriate label attached thereto before removal of the label moiety and the subsequent next round of sequencing.

In order to ensure that only a single incorporation occurs during a cycle, a structural modification ("protecting group" or "blocking group") is included in each labeled nucleotide that is added to the growing chain to ensure that only one nucleotide is incorporated. After the modified nucleotide, often referred to as a fully functional nucleotide (ffN), has been added, the blocking group is then removed under reaction conditions which do not interfere with the integrity of the DNA being sequenced. The sequencing cycle can then continue with the incorporation of the next blocked, labeled nucleotide.

The shipping and storage of reagents used in SBS methods at ambient temperatures is desirable as it reduces the reliance on resources. Some SBS reagents, however, have reduced stability at ambient temperatures. Some ffNs are less stable at ambient temperatures and the blocking group is lost, resulting in a degraded ffN. The resulting unblocked nucleotide is recognized by the polymerase and can be incorporated during a sequencing reaction, but the absence of the blocking group allows the next nucleotide to be incorporated, which increases pre-phasing. Pre-phasing is highly undesirable as it increases noise, reduces sequencing quality, and reduces read length during a sequencing run.

SUMMARY OF THE APPLICATION

Provided herein are recombinant DNA polymerases having improved resistance to recognizing and incorporating nucleotides that have degraded and no longer include a blocking group. In some embodiments, the recombinant DNA polymerases herein also provide improved read length.

One example of a polymerase of the present disclosure includes an amino acid sequence that is at least 80% identical to a DNA polymerase amino acid sequence SEQ ID NO:8 or 12, where the recombinant DNA polymerase includes at least one, at least two, or at least three amino acid substitution mutations at positions functionally equivalent to an amino acid selected from Ala408, Ala409, and Ile410 in the polymerase amino acid sequence. In one embodiment, the substitution mutation at the position functionally equivalent to Ala408 is a mutation to a polar or uncharged amino acid, such as Tyr. In one embodiment, the substitution mutation at the position functionally equivalent to Ala409 is a mutation to a non-polar or hydrophobic amino acid, such as Pro. In one embodiment, the substitution mutation at the position functionally equivalent to Ile410 is a mutation to a non-polar or hydrophobic amino acid, such as Ala or Pro. In one embodiment, a polymerase further includes at least one, at least two, at least three, at least four, at least five, at least six, at least seven, at least eight, or at least nine amino acid substitution mutations at positions functionally equivalent to an amino acid selected from Ala129, Ala141, Ala143, Ser223, Val485, Gly497, Tyr247, Asp599, and Gly633 in the polymerase amino acid sequence.

Also provided is a nucleic acid molecule encoding a polymerase described herein, an expression vector that includes the nucleic acid molecule, and a host cell that includes the vector.

Further provided are methods. In one embodiment, a method is for incorporating modified nucleotides into DNA, and includes allowing the following components to interact: (i) a polymerase described herein, (ii) a DNA template; and (iii) a nucleotide solution.

Also provided are kits. In one embodiment, a kit is for performing a nucleotide incorporation reaction. The kit can include a polymerase described herein and a nucleotide solution.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The term "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Conditions that are "suitable" for an event to occur or "suitable" conditions are conditions that do not prevent such events from occurring. Thus, these conditions permit, enhance, facilitate, and/or are conducive to the event.

As used herein, "providing" in the context of a composition, an article, a nucleic acid, or a nucleus means making the composition, article, nucleic acid, or nucleus, purchasing the composition, article, nucleic acid, or nucleus, or otherwise obtaining the compound, composition, article, or nucleus.

Also as used herein, the recitations of numerical ranges by endpoints include all numbers subsumed within that range (e.g., 1 to 5 includes 1, 1.5, 2, 2.75, 3, 3.80, 4, 5, etc.).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

BRIEF DESCRIPTION OF THE FIGURES

The following detailed description of illustrative embodiments of the present disclosure may be best understood when read in conjunction with the following drawings.

FIG. 1 is a schematic showing alignment of polymerase amino acid sequences from *Thermococcus* sp. 9°N-7 (9°N, SEQ ID NO:1), *Thermococcus litoralis* (Vent, SEQ ID NO:2 and Deep Vent, SEQ ID NO:3), *Thermococcus waiotapuensis* (Twa, SEQ ID NO:7), *Thermococcus kodakaraensis* (KOD, SEQ ID NO:5), *Pyrococcus furiosus* (Pfu, SEQ ID NO:4), *Pyrococcus abyssi* (Pab, SEQ ID NO:6). An "*" (asterisk) indicates positions which have a single, fully conserved residue between all polymerases. A ":" (colon) indicates conservation between groups of strongly similar properties as below—roughly equivalent to scoring >0.5 in the Gonnet PAM 250 matrix. A "." (period) indicates conservation between groups of weakly similar properties as below—roughly equivalent to scoring=<0.5 and >0 in the Gonnet PAM 250 matrix.

Figure 2:
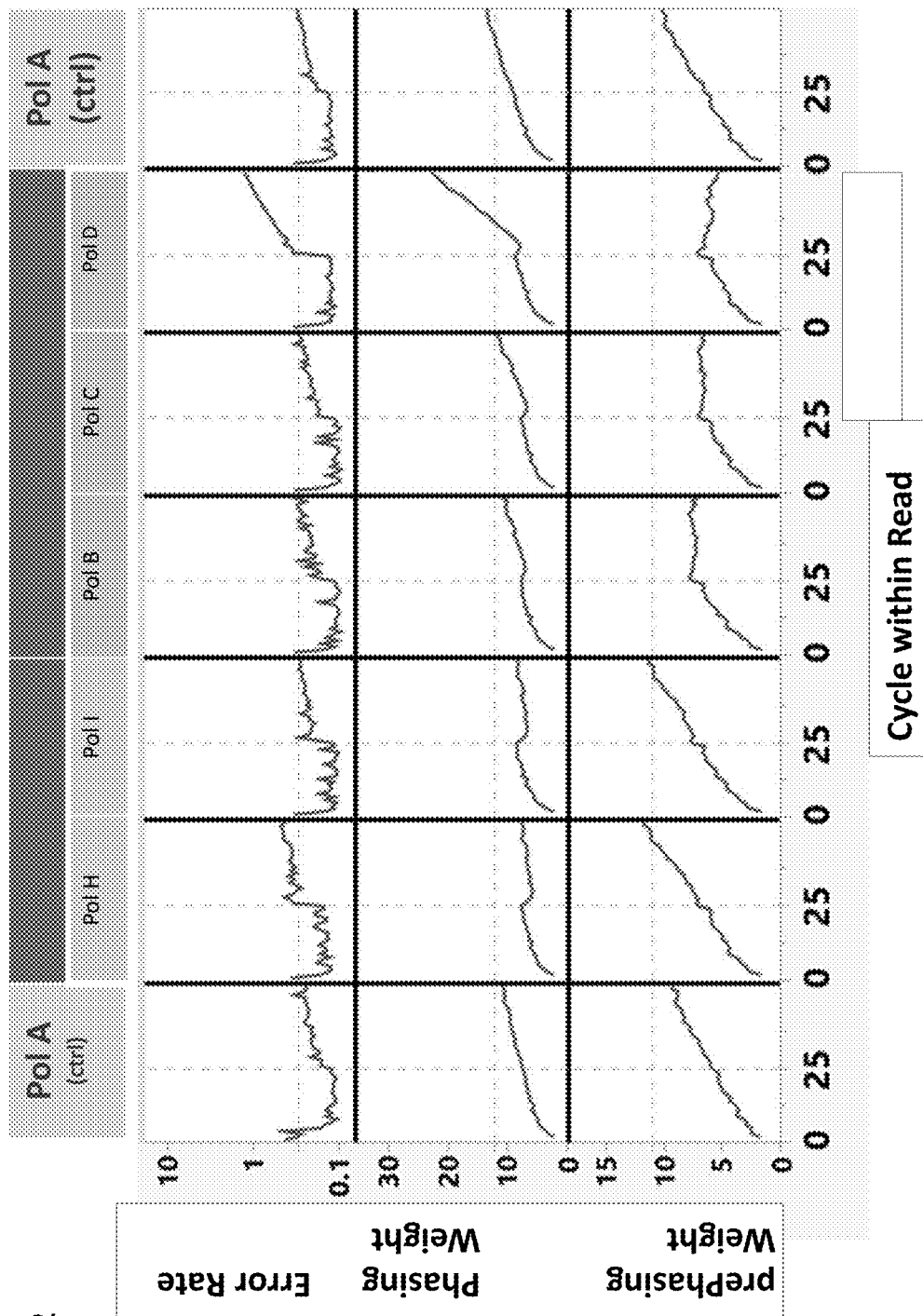
FIG. 2 shows the error rates, phasing levels, and pre-phasing levels of selected altered polymerases of the present disclosure. "Pol A" identifies a polymerase having SEQ ID NO:1 with the following substitution mutations: Met129Ala, Asp141Ala, Glu143Ala, Cys223Ser, Leu408Ala, Tyr409Ala, Pro410Ile, Ala485Val; Pol H is SEQ ID NO:12 with substitution mutation Tyr291Cys; Pol I is SEQ ID NO:12 with substitution mutation Gly427Glu; Pol B is SEQ ID NO:24; Pol C is SEQ ID NO:24 with substitution mutations Tyr291Cys and Gly427Glu; Pol D is SEQ ID NO:24 with substitution mutations Tyr291Cys, Gly427Glu, and Ala485Gly; "Error Rate," "Phasing weight," and "pre-Phasing weight" refer to error rate, phasing rate, and pre-phasing rates during Read 1.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION OF ILLUSTRATIVE EMBODIMENTS

Maintaining or surpassing current levels of performance when using modified nucleotides that have been stored at ambient temperatures can be aided by a new generation of polymerases. Presented herein are polymerase enzymes having significantly improved performance under SBS conditions when using ambiently-stored modified nucleotides. The inventors have identified mutations that confer on polymerases a resistance to incorporating nucleotides that have lost the blocking group. The types of mutations conferring this type of activity were surprising. Some mutations were also found to improve read length.

Phasing and pre-phasing are terms known to those of skill in the art and are used to describe the loss of synchrony in the readout of the sequence copies of a cluster. Phasing and pre-phasing cause the extracted intensities for a specific cycle to include the signal of the current cycle and noise from the preceding and following cycles. Thus, as used herein, the term "phasing" refers to a phenomenon in SBS that is caused by incomplete incorporation of a nucleotide in some portion of DNA strands within clusters by polymerases at a given sequencing cycle and is thus a measure of the rate at which single molecules within a cluster lose sync with each other. Phasing can be measured during detection of cluster signal at each cycle and can be reported as a percentage of detectable signal from a cluster that is out of synchrony with the signal in the cluster. As an example, a cluster is detected by a "green" fluorophore signal during cycle N. In the subsequent cycle (cycle N+1), 99.9% of the cluster signal is detected in the "red" channel and 0.1% of the signal remains from the previous cycle and is detected in the "green" channel. This result would indicate that phasing is occurring, and can be reported as a numerical value, such as a phasing value of 0.1, indicating that 0.1% of the molecules in the cluster are falling behind at each cycle.

The term "pre-phasing" as used herein refers to a phenomenon in SBS that is caused by the incorporation of nucleotides without effective 3' terminators, causing the incorporation event to go one cycle ahead. As the number of cycles increases, the fraction of sequences per cluster affected by pre-phasing increases, hampering the identification of the correct base. Pre-phasing can be detected by a sequencing instrument and reported as a numerical value, such as a pre-phasing value of 0.1, indicating that 0.1% of the molecules in the cluster are running ahead at each cycle.

Detection of phasing and pre-phasing can be performed and reported according to any suitable methodology as is known in the art, for example, as described in U.S. Pat. No. 8,965,076 and U.S. Patent Application Publication No 2018/0057018. Pre-phasing can be detected and reported routinely during SBS sequencing runs on sequencing instrument such as HiSeq™, Genome Analyzer™, NextSeq™, NovaSeq™, iSeq™, MiniSeq™, or MiSeq™ sequencing platforms from Illumina, Inc. (San Diego, CA) or any other suitable instrument known in the art.

Error rate refers to a measurement of the frequency of error in the identification of the correct base, i.e., the complement of the template sequence at a specific position, during a sequencing reaction. The fidelity with which a sequenced library matches the original genome sequence can vary depending on the frequency of base mutation occurring at any stage from the extraction of the nucleic acid to its sequencing on a sequencing platform. This frequency places an upper limit on the probability of a sequenced base being correct. In some embodiments, the quality score is presented as a numerical value. For example, the quality score can be quoted as QXX where the XX is the score and it means that that particular call has a probability of error of $10^{-XX/10}$. Thus, as an example, Q30 equates to an error rate of 1 in 1000, or 0.1%, and Q40 equates to an error rate of 1 in 10,000, or 0.01%.

The shipment of reagents for sequencing reactions at ambient temperatures is highly desirable but can result in the degradation of modified nucleotides by loss of the blocking group. The use of degraded nucleotides, however, in sequencing reactions can increase the occurrence of pre-phasing, which contributes to error rate. The discovery of altered polymerases which decrease pre-phasing in the presence of degraded nucleotides is unexpected and provides the advantage of shipping and storing reagents at ambient temperatures.

Polymerases

Provided herein are polymerases, compositions including a polymerase, and methods of using a polymerase. A polymerase described herein is a DNA polymerase. In one embodiment, a polymerase of the present disclosure, also referred to herein interchangeably as an "altered polymerase" and a "recombinant polymerase," is based on the amino acid sequence of a reference polymerase. An altered polymerase includes substitution mutations at one or more residues when compared to the reference polymerase. A substitution mutation can be at the same position or a functionally equivalent position compared to the reference polymerase. Reference polymerases and functionally equivalent positions are described in detail herein. The skilled person will readily appreciate that an altered polymerase described herein is not naturally occurring.

A reference polymerase described herein incorporates nucleotides during a SBS reaction at rates that are useful in SBS reactions; however, the reference polymerases also incorporate nucleotides that have lost the blocking group at a rate similar to the rate of incorporation of nucleotides containing the blocking group, e.g., the reference polymerases do not distinguish between the two types of nucleotides. In contrast, the altered polymerases described herein maintain the superior incorporation rates of modified nucleotides observed with reference polymerases but have the advantage of reduced incorporation rates of nucleotides that have lost the blocking group. Methods for determining if an altered polymerase has different incorporation rates for modified and degraded nucleotides can be found in the Examples.

In one embodiment, reduced pre-phasing rates occur when the altered polymerase is tested using fast incorporation times. Incorporation refers to the amount of time a DNA polymerase is in contact with a template. As used herein, a slow incorporation time is the incorporation time used under a standard cycle using a MiniSeq™ benchtop sequencing system. Slow incorporation times include from 40 seconds to 100 seconds. As used herein, a fast cycle time refers to an incorporation step that is from 10 seconds to 40 seconds.

An altered polymerase described herein can be used in SBS reactions for runs of different lengths. A "run" refers to the number of nucleotides that are identified on a template. A run typically includes a run based on the first primer (e.g., a read1 primer) which reads one strand of a template and a run based on the second primer (e.g., a read2 primer) which reads the complementary strand of the template. In one embodiment, the number of nucleotides identified using the first primer or the second primer can be from 10 to 300 nucleotides. In one embodiment, the number of nucleotides identified using the first primer or the second primer can be no greater than 300 nucleotides, no greater than 260 nucleotides, no greater than 240 nucleotides, no greater than 200 nucleotides, no greater than 160 nucleotides, no greater than 120 nucleotides, no greater than 80 nucleotides, or no greater than 40 nucleotides. In one embodiment, the number of nucleotides identified using the first primer or the second primer can be at least 10, at least 40, at least 80, at least 120, at least 160, at least 200, at least 240, at least 260, or at least 300 nucleotides.

In certain embodiments, an altered polymerase is based on a family B type DNA polymerase. An altered polymerase can be based on, for example, a family B archaeal DNA polymerase, a human DNA polymerase-α, or a phage polymerase.

Family B archaeal DNA polymerases are well known in the art as exemplified by the disclosure of U.S. Pat. No. 8,283,149. In certain embodiments, an archaeal DNA polymerase is from a hyperthermophilic archaeon and is thermostable.

In certain embodiments, a family B archaeal DNA polymerase is from a genus such as, for example, *Thermococcus, Pyrococcus, Methanococcus, Pyrobaculum, Pyrodictium occultum*, and *Aeropyrum pernix*. Members of the genus *Thermococcus* are well known in the art and include, but are not limited to *T.* 4557, *T. barophilus, T. gammatolerans, T. onnurineus, T. sibiricus, T. kodakarensis, T. gorgonarius* (TGO), and *T. waiotapuensis*. Members of the genus *Pyrococcus* are well known in the art and include, but are not limited to *P.* NA2, *P. abyssi, P. furiosus, P. horikoshii, P. yayanosii, P. endeavori, P. glycovorans*, and *P. woesei*. Members of the genus *Methanococcus* are well known in the art and include, but are not limited to *M. aeolicus, M. maripaludis, M. vannielii, M. voltae, M. thermolithotrophicus*, and *M. jannaschii*. Members of the genus *Pyrobaculum* are well known in the art and include, but are not limited to, *P. calidifontis* (Pc). Members of the genus *Pyrodictium* are well known in the art and include, but are not limited to, *P. occultum*. Members of the genus *Aeropyrum* are well known in the art and include, but are not limited to, *A. pernix*.

In one embodiment an altered polymerase is based on Vent, Deep Vent®, 9°N, Pfu, KOD, or a Pab polymerase. Vent® and Deep Vent® are commercial names used for family B DNA polymerases isolated from the hyperthermophilic archaeon *Thermococcus litoralis*. 9°N polymerase is a family B polymerase isolated from *Thermococcus* sp. Pfu polymerase is a family B polymerase isolated from *Pyrococcus furiosus*. KOD polymerase is a family B polymerase isolated from *Thermococcus kodakaraenis*. Pab polymerase is a family B polymerase isolated from *Pyrococcus abyssi*. Twa is a family B polymerase isolated from *T. waiotapuensis*. Examples of Vent®, Deep Vent®, 9°N, Pfu, KOD, Pab, and Twa polymerases are disclosed in FIG. 1.

In certain embodiments, a family B DNA polymerase is from a phage such as, for example, T4, RB69, or phi29 phage.

FIG. 1 shows a sequence alignment for proteins having the amino acid sequences shown in SEQ ID NOs:1-7. The alignment indicates amino acids that are conserved in the different family B polymerases. The skilled person will appreciate that the conserved amino acids and conserved regions are most likely conserved because they are important to the function of the polymerases, and therefore show a correlation between structure and function of the polymerases. The alignment also shows regions of variability across the different family B polymerases. A person of ordinary skill in the art can deduce from such data regions of a polymerase in which substitutions, particularly conservative substitutions, may be permitted without unduly affecting biological activity of the altered polymerase.

An altered polymerase described herein is based on the amino acid sequence of a known polymerase (also referred to herein as a reference polymerase) and further includes substitution mutations at one or more residues. In one embodiment, a substitution mutation is at a position functionally equivalent to an amino acid of a reference polymerase. By "functionally equivalent" it is meant that the altered polymerase has the amino acid substitution at the amino acid position in the reference polymerase that has the same functional role in both the reference polymerase and the altered polymerase.

In general, functionally equivalent substitution mutations in two or more different polymerases occur at homologous amino acid positions in the amino acid sequences of the polymerases. Hence, use herein of the term "functionally equivalent" also encompasses mutations that are "positionally equivalent" or "homologous" to a given mutation, regardless of whether or not the particular function of the mutated amino acid is known. It is possible to identify the locations of functionally equivalent and positionally equivalent amino acid residues in the amino acid sequences of two or more different polymerases on the basis of sequence alignment and/or molecular modelling. An example of sequence alignment to identify positionally equivalent and/or functionally equivalent residues is set forth in FIG. 1. For example, the residues in the Twa, KOD, Pab, Pfu, Deep Vent®, and Vent® polymerases of FIG. 1 that are vertically aligned are considered positionally equivalent as well as functionally equivalent to the corresponding residue in the 9°N polymerase amino acid sequence. Thus, for example residue 349 of the 9°N, Twa, KOD, Pfu, Deep Vent®, and Pab polymerases and residue 351 of the Vent® polymerase are functionally equivalent and positionally equivalent. Likewise, for example residue 633 of the 9°N, Twa, KOD, and Pab polymerases, residue 634 of the Pfu and Deep Vent® polymerases, and residue 636 of the Vent® polymerase are functionally equivalent and positionally equivalent. The skilled person can easily identify functionally equivalent residues in DNA polymerases.

In certain embodiments, the substitution mutation comprises a mutation to a residue having a non-polar side chain. Amino acids having non-polar side chains are well-known in the art and include, for example: alanine, glycine, isoleucine, leucine, methionine, phenylalanine, proline, tryptophan, and valine.

In certain embodiments, the substitution mutation comprises a mutation to a residue having a polar side chain. Amino acids having polar side chains are well-known in the art and include, for example: arginine, asparagine, aspartic acid, glutamine, glutamic acid, histidine, lysine, serine, cysteine, tyrosine, and threonine.

In certain embodiments, the substitution mutation comprises a mutation to a residue having a hydrophobic side chain. Amino acids having hydrophobic side chains are well-known in the art and include, for example: glycine, alanine, valine, leucine, isoleucine, proline, phenylalanine, methionine, and tryptophan.

In certain embodiments, the substitution mutation comprises a mutation to a residue having an uncharged side chain. Amino acids having uncharged side chains are well-known in the art and include, for example: glycine, serine, cysteine, asparagine, glutamine, tyrosine, and threonine, among others.

In one embodiment, an altered polymerase has an amino acid sequence that is structurally similar to a reference polymerase disclosed herein. In one embodiment, the reference polymerase is SEQ ID NO:1 with the following substitution mutations: Met129Ala, Asp141Ala, Glu143Ala, Cys223Ser, Leu408Ala, Tyr409Ala, Pro410Ile, Ala485Val, and Tyr497Gly, and at least one substitution mutation chosen from Arg247Tyr, Glu599Asp, Lys620Arg, His633Gly, and Val661Asp. An example of a reference polymerase is SEQ ID NO:1 with the following substitution mutations: Met129Ala, Asp141Ala, Glu143Ala, Cys223Ser, Leu408Ala, Tyr409Ala, Pro410Ile, Ala485Val, Tyr497Gly, Arg247Tyr, Glu599Asp, and His633Gly. This second reference polymerase is disclosed at SEQ ID NO:8.

Another example of a reference sequence is SEQ ID NO:1 with the following substitution mutations: Met129Ala, Asp141Ala, Glu143Ala, Cys223Ser, Leu408Ala, Tyr409Ala, Pro410Ile, Ala485Val, Tyr497Gly, Arg247Tyr, His633Gly, and Val661Asp. This reference polymerase is disclosed at SEQ ID NO:9

Another example of a reference sequence is SEQ ID NO:1 with the following substitution mutations: Met129Ala, Asp141Ala, Glu143Ala, Cys223Ser, Leu408Ala, Tyr409Ala, Pro410Ile, Ala485Val, Tyr497Gly, Arg247Tyr, Glu599Asp, Lys620Arg, and His633Gly. This reference polymerase is disclosed at SEQ ID NO:10.

Another example of a reference sequence is SEQ ID NO:1 with the following substitution mutations: Met129Ala, Asp141Ala, Glu143Ala, Cys223Ser, Leu408Ala, Tyr409Ala, Pro410Ile, Ala485Val, Tyr497Gly, Arg247Tyr, and His633Gly. This reference polymerase is disclosed at SEQ ID NO:11.

In another embodiment, the reference polymerase is SEQ ID NO: 1 with the following substitution mutations: Met129Ala, Asp141Ala, Glu143Ala, Cys223Ser, Leu408Ala, Tyr409Ala, Pro410Ile, Ala485Val, and Tyr497Gly, and at least one substitution mutation chosen from Ala281Phe, Phe283Ser, Thr349Lys, Thr349Ser, Thr349Asn, Trp397Cys, and His633Thr. An example of a reference polymerase is SEQ ID NO:1 with the following substitution mutations: Met129Ala, Asp141Ala, Glu143Ala, Cys223Ser, Leu408Ala, Tyr409Ala, Pro410Ile, Ala485Val, Tyr497Gly, Arg247Tyr, Glu599Asp, His633Gly, and Thr349Lys. This reference polymerase is disclosed at SEQ ID NO:12.

Another example of a reference sequence is SEQ ID NO:1 with the following substitution mutations: Met129Ala, Asp141Ala, Glu143Ala, Cys223Ser, Leu408Ala, Tyr409Ala, Pro410Ile, Ala485Val, Tyr497Gly, Arg247Tyr, Glu599Asp, His633Gly, and Ala281Phe. This reference polymerase is disclosed at SEQ ID NO:13.

Another example of a reference sequence is SEQ ID NO:1 with the following substitution mutations: Met129Ala, Asp141Ala, Glu143Ala, Cys223Ser, Leu408Ala, Tyr409Ala, Pro410Ile, Ala485Val, Tyr497Gly, Arg247Tyr, Glu599Asp, His633Gly, and Phe283Ser. This reference polymerase is disclosed at SEQ ID NO:14.

Another example of a reference sequence is SEQ ID NO:1 with the following substitution mutations: Met129Ala, Asp141Ala, Glu143Ala, Cys223 Ser, Leu408Ala, Tyr409Ala, Pro410Ile, Ala485Val, Tyr497Gly, Arg247Tyr, Glu599Asp, His633Gly, and Thr349Ser. This reference polymerase is disclosed at SEQ ID NO:15.

Another example of a reference sequence is SEQ ID NO:1 with the following substitution mutations: Met129Ala, Asp141Ala, Glu143Ala, Cys223Ser, Leu408Ala, Tyr409Ala, Pro410Ile, Ala485Val, Tyr497Gly, Arg247Tyr, Glu599Asp, His633Gly, and Thr349Asn. This reference polymerase is disclosed at SEQ ID NO:16.

Another example of a reference sequence is SEQ ID NO:1 with the following substitution mutations: Met129Ala, Asp141Ala, Glu143Ala, Cys223Ser, Leu408Ala, Tyr409Ala, Pro410Ile, Ala485Val, Tyr497Gly, Arg247Tyr, Glu599Asp, His633Gly, Thr349Lys, and Trp397Cys. This reference polymerase is disclosed at SEQ ID NO:17.

Another example of a reference sequence is SEQ ID NO:1 with the following substitution mutations: Met129Ala, Asp141Ala, Glu143Ala, Cys223Ser, Leu408Ala, Tyr409Ala, Pro410Ile, Ala485Val, Tyr497Gly, Arg247Tyr, Glu599Asp, and His633Thr. This reference polymerase is disclosed at SEQ ID NO:18.

Other reference sequences include SEQ ID NO:2, 3, 4, 5, 6, or 7 with substitution mutations described herein. In one embodiment, other reference sequences include SEQ ID NO:2, 3, 4, 5, 6, or 7 with substitution mutations functionally equivalent to the following substitution mutations in the wild-type 9°N polymerase (SEQ ID NO:1): Met129Ala, Asp141Ala, Glu143Ala, Cys223Ser, Leu408Ala, Tyr409Ala, Pro410Ile, Ala485Val, and Tyr497Gly, and at least one substitution mutation chosen from Arg247Tyr, Glu599Asp, Lys620Arg, His633Gly, and Val661Asp. In another embodiment, other reference sequences include SEQ ID NO:2, 3, 4, 5, 6, or 7 with substitution mutations functionally equivalent to the following substitution mutations in the wild-type 9°N polymerase (SEQ ID NO:1): Met129Ala, Asp141Ala, Glu143Ala, Cys223Ser, Leu408Ala, Tyr409Ala, Pro410Ile, Ala485Val, and Tyr497Gly, and at least one substitution mutation chosen from Ala281Phe, Phe283Ser, Thr349Lys, Thr349Ser, Thr349Asn, Trp397Cys, and His633Thr.

As used herein, an altered polymerase may be "structurally similar" to a reference polymerase if the amino acid sequence of the altered polymerase possesses a specified amount of sequence similarity and/or sequence identity compared to the reference polymerase.

Structural similarity of two amino acid sequences can be determined by aligning the residues of the two sequences (for example, a candidate polymerase and a reference polymerase described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate polymerase is the polymerase being compared to the reference polymerase. A candidate polymerase that has structural similarity with a reference polymerase and polymerase activity is an altered polymerase.

Unless modified as otherwise described herein, a pairwise comparison analysis of amino acid sequences or nucleotide sequences can be conducted, for instance, by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Current Protocols in Molecular Biology, Ausubel et al., eds., Current Protocols, a joint venture between Greene Publishing Associates, Inc. and John Wiley & Sons, Inc., supplemented through 2004).

One example of an algorithm that is suitable for determining structural similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., J. Mol. Biol. 215:403-410 (1990)). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a protein may be selected from other members of the class to which the amino acid belongs. For example, it is well-known in the art of protein biochemistry that an amino acid belonging to a grouping of amino acids having a particular size or characteristic (such as charge, hydrophobicity, or hydrophilicity) can be substituted for another amino acid without altering the activity of a protein, particularly in regions of the protein that are not directly associated with biological activity. For example, non-polar amino acids include alanine, glycine, isoleucine, leucine, methionine, phenylalanine, proline, tryptophan, and valine. Hydrophobic amino acids include glycine, alanine, valine, leucine, isoleucine, proline, phenylalanine, methionine, and tryptophan. Polar amino acids include arginine, asparagine, aspartic acid, glutamine, glutamic acid, histidine, lysine, serine, cysteine, tyrosine, and threonine. The uncharged amino acids include glycine, serine, cysteine, asparagine, glutamine, tyrosine, and threonine, among others.

Thus, reference to a polymerase, such as reference to the amino acid sequence of one or more SEQ ID NOs described herein can include a protein with at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to the reference polymerase.

Alternatively, reference to a polymerase, such as reference to the amino acid sequence of one or more SEQ ID NOs described herein can include a protein with at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference polymerase.

The present disclosure describes a collection of mutations that result in a polymerase having one or more of the activities described herein. A polymerase described herein can include any number of substitution mutations, e.g., at least 1, at least 2, at least 3, at least 4, at least 5, at least 6, at least 7, at least 8, at least 9, at least 10, at least 11, at least 12, at least 13, at least 14, at least 15, at least 16, at least 17, or at least 18 mutations compared to a reference polymerase, such as SEQ ID NO:8, 9, 10, 11, 12, 13, 14, 15, 16, 17, or 18. Likewise, a polymerase described herein can include the mutations in any combination.

In one embodiment, an altered polymerase includes a substitution mutation at a position functionally equivalent to Ala408 in a 9°N polymerase (e.g., reference polymerase SEQ ID NO:8 or 12). In one embodiment, the substitution mutation at a position functionally equivalent to Ala408 is a mutation to a polar or uncharged amino acid, for example Tyr.

In one embodiment, an altered polymerase includes a substitution mutation at a position functionally equivalent to Ala409 in a 9°N polymerase (e.g., reference polymerase SEQ ID NO:8 or 12). In one embodiment, the substitution mutation at a position functionally equivalent to Ala409 is a mutation to a non-polar or hydrophobic amino acid, for example Pro.

In one embodiment, an altered polymerase includes a substitution mutation at a position functionally equivalent to Ile410 in a 9°N polymerase (e.g., reference polymerase SEQ ID NO:8 or 12). In one embodiment, the substitution mutation at a position functionally equivalent to Ile410 is a mutation to a non-polar or hydrophobic amino acid, for example Ala or Pro.

An altered polymerase of the present disclosure includes substitution mutations at positions functionally equivalent to Ala408 and Ala409, or Ala409 and Ile410, or Ala408 and Ile410, or at all three positions. In one embodiment, an altered polymerase is SEQ ID NO:8 with the following substitution mutations: Ala408Tyr, Ala409Pro, and Pro410Ala (SEQ ID NO:19), Ala408Tyr and Ala409Pro (SEQ ID NO:20), or Ala408Tyr, Ala409Pro, and Ile410Pro (SEQ ID NO:21). In one embodiment, an altered polymerase is SEQ ID NO:12 with the following substitution mutations: Ala408Tyr, Ala409Pro, and Pro410Ala (SEQ ID NO:22), Ala408Tyr and Ala409Pro (SEQ ID NO:23), or Ala408Tyr, Ala409Pro, and Ile410Pro (SEQ ID NO:24).

An altered polymerase of the present disclosure, e.g., a polymerase having an amino acid sequence of SEQ ID NO:8 or 12 and a substitution mutation at a position functionally equivalent to Ala408, Ala409, Ile410, or a combination thereof, can further include one or more additional substitution mutations.

In one embodiment, the substitution mutation is at a position functionally equivalent to Ala129 in a reference polymerase, such as SEQ ID NO:8 or 12. In one embodiment, the substitution mutation at a position functionally equivalent to Ala129 in SEQ ID NO:8 or 12 is a mutation to a non-polar or hydrophobic amino acid. In one embodiment, the substitution mutation is a mutation to alanine, cysteine, glycine, isoleucine, leucine, phenylalanine, proline, tryptophan, tyrosine, or valine. In one embodiment, the substitution mutation is a mutation to any amino acid other than methionine.

In one embodiment, the substitution mutation is at a position functionally equivalent to Ala141 in a reference polymerase, such as SEQ ID NO:8 or 12. In one embodiment, the substitution mutation at a position functionally equivalent to Ala141 in SEQ ID NO:8 or 12 is a mutation to a non-polar or hydrophobic amino acid.

In one embodiment, the substitution mutation is at a position functionally equivalent to Ala143 in a reference polymerase, such as SEQ ID NO:8 or 12. In one embodiment, the substitution mutation at a position functionally equivalent to Ala143 in SEQ ID NO:8 or 12 is a mutation to a non-polar or hydrophobic amino acid.

In one embodiment, the substitution mutation is at a position functionally equivalent to Ser223 in a reference polymerase, such as SEQ ID NO:8 or 12. In one embodiment, the substitution mutation at a position functionally equivalent to Ser223 in SEQ ID NO:8 or 12 is a mutation to a polar or uncharged amino acid.

In one embodiment, the substitution mutation is at a position functionally equivalent to Val485 in a reference polymerase, such as SEQ ID NO:8 or 12. In one embodiment, the substitution mutation at a position functionally equivalent to Val485 in SEQ ID NO:8 or 12 is a mutation to a non-polar or hydrophobic amino acid, such as Gly.

In one embodiment, the substitution mutation is at a position functionally equivalent to Gly497 in a reference polymerase, such as SEQ ID NO:8 or 12. In one embodiment, the substitution mutation at a position functionally equivalent to Gly497 in SEQ ID NO:8 or 12 is a mutation to a non-polar, hydrophobic, or uncharged amino acid.

In one embodiment, the substitution mutation is at a position functionally equivalent to Tyr247 in a reference polymerase, such as SEQ ID NO:8 or 12. In one embodiment, the substitution mutation at a position functionally equivalent to Tyr247 in SEQ ID NO:8 or 12 is a mutation to a polar or uncharged amino acid.

In one embodiment, the substitution mutation is at a position functionally equivalent to Asp599 in a reference polymerase, such as SEQ ID NO:8 or 12. In one embodiment, the substitution mutation at a position functionally equivalent to Asp599 in SEQ ID NO:8 or 12 is a mutation to a polar amino acid.

In one embodiment, the substitution mutation is at a position functionally equivalent to Gly633 in a reference polymerase, such as SEQ ID NO:8 or 12. In one embodiment, the substitution mutation at a position functionally equivalent to Gly633 in SEQ ID NO:8 or 12 is a mutation to a non-polar, hydrophobic, or uncharged amino acid.

In one embodiment, the substitution mutation is at a position functionally equivalent to Lys349 in a reference polymerase, such as SEQ ID NO:12. In one embodiment, the substitution mutation at a position functionally equivalent to Lys349 is a mutation to a polar or uncharged amino acid, such as Ser or Arg.

In one embodiment, an altered polymerase of the present disclosure includes at least one, at least two, at least three, at least four, at least five, at least six, at least seven, at least eight, or at least nine, substitution mutations at a position functionally equivalent to Ala129, Ala 141, Ala143, Ser223, Val485, Gly497, Tyr247, Asp599, or Gly633 in a reference polymerase such as SEQ ID NO:8. In one embodiment, an altered polymerase of the present disclosure includes at least one, at least two, at least three, at least four, at least five, at least six, at least seven, at least eight, at least nine, or at least ten substitution mutations at a position functionally equivalent to Ala129, Ala 141, Ala 143, Ser223, Val485, Gly497, Tyr247, Asp599, Gly633, or Lys349 in a reference polymerase such as SEQ ID NO:12.

In another embodiment, an altered polymerase described herein can further include one or more additional substitution mutations selected from a position functionally equivalent to Lys620 or Val661 in a reference polymerase, such as SEQ ID NO:8 or 12.

In one embodiment, the substitution mutation is at a position functionally equivalent to Lys620 in a reference polymerase, such as SEQ ID NO:8 or 12, is a mutation to a polar or uncharged amino acid, for example, Arg.

In one embodiment, the substitution mutation is at a position functionally equivalent to Val661 in a reference polymerase, such as SEQ ID NO:8 or 12, is a mutation to a polar amino acid, for example, Asn.

In other embodiments, an altered polymerase described herein can further include one or more additional substitution mutations chosen from a position functionally equivalent to Phe152, Val278, Met329, Val471, Thr514, Leu631, Glu734, Lys476, Lys477, Ile521, and Thr590 in a reference polymerase, such as SEQ ID NO:8 or 12.

In one embodiment, the substitution mutation is at a position functionally equivalent to Phe152 in a reference polymerase, such as SEQ ID NO:8 or 12. In one embodiment, the substitution mutation at a position functionally equivalent to Phe152 in SEQ ID NO:8 or 12 is a mutation to a non-polar, hydrophobic, or uncharged amino acid, for example Gly.

In one embodiment, the substitution mutation is at a position functionally equivalent to Val278 in a reference polymerase, such as SEQ ID NO:8 or 12. In one embodiment, the substitution mutation at a position functionally equivalent to Val278 in SEQ ID NO:8 or 12 is a mutation to a non-polar or hydrophobic amino acid, for example Leu.

In one embodiment, the substitution mutation is at a position functionally equivalent to Met329 in a reference polymerase, such as SEQ ID NO:8 or 12. In one embodiment, the substitution mutation at a position functionally equivalent to Met329 in SEQ ID NO:8 or 12 is a mutation to a polar amino acid, for example His.

In one embodiment, the substitution mutation is at a position functionally equivalent to Val471 in a reference polymerase, such as SEQ ID NO:8 or 12. In one embodiment, the substitution mutation at a position functionally equivalent to Val471 in SEQ ID NO:8 or 12 is a mutation to a polar or uncharged amino acid, for example Ser.

In one embodiment, the substitution mutation is at a position functionally equivalent to Thr514 in a reference polymerase, such as SEQ ID NO:8 or 12. Polymerases including a substitution mutation at a position functionally equivalent to Thr514 in a 9°N polymerase (SEQ ID NO:1) are known in the art and exemplified by U.S. Patent Application No. 2016/0032377. In one embodiment, the substitution mutation at a position functionally equivalent to Thr514 in SEQ ID NO:8 or 12 is a mutation to a non-polar or hydrophobic amino acid, for example Ala. In some embodiments, other substitution mutations that can be used in combination with a non-polar or hydrophobic amino acid at a position functionally equivalent to Thr514 include Phe152, Val278, Met329, Val471, Leu631, Glu734, or a combination thereof. In one embodiment, the substitution mutation at a position functionally equivalent to Thr514 is a mutation to a polar or uncharged amino acid, for example Ser. In some embodiments, other substitution mutations that can be used in combination with a polar or uncharged amino acid at a position functionally equivalent to Thr514 include Lys476, Lys477, Ile521, Thr590, or a combination thereof.

In one embodiment, the substitution mutation is at a position functionally equivalent to Leu631 in a reference polymerase, such as SEQ ID NO:8 or 12. In one embodiment, the substitution mutation at a position functionally equivalent to Leu631 in SEQ ID NO:8 or 12 is a mutation to a non-polar or hydrophobic amino acid, for example Met.

In one embodiment, the substitution mutation is at a position functionally equivalent to Glu734 in a reference polymerase, such as SEQ ID NO:8 or 12. In one embodiment, the substitution mutation at a position functionally equivalent to Glu734 in SEQ ID NO:8 or 12 is a mutation to a polar or uncharged amino acid, for example Arg.

In one embodiment, the substitution mutation is at a position functionally equivalent to Lys476 in a reference polymerase, such as SEQ ID NO:8 or 12. In one embodiment, the substitution mutation at a position functionally equivalent to Lys476 in SEQ ID NO:8 or 12 is a mutation to a non-polar or hydrophobic amino acid, for example Trp.

In one embodiment, the substitution mutation is at a position functionally equivalent to Lys477 in a reference polymerase, such as SEQ ID NO:8 or 12. In one embodiment, the substitution mutation at a position functionally equivalent to Lys477 in SEQ ID NO:8 or 12 is a mutation to a non-polar or hydrophobic amino acid, for example Met.

In one embodiment, the substitution mutation is at a position functionally equivalent to Ile521 in a reference polymerase, such as SEQ ID NO:8 or 12. In one embodiment, the substitution mutation at a position functionally equivalent to Ile521 in SEQ ID NO:8 or 12 is a mutation to a non-polar amino acid, for example Leu.

In one embodiment, the substitution mutation is at a position functionally equivalent to Thr590 in a reference polymerase, such as SEQ ID NO:8 or 12. In one embodiment, the substitution mutation at a position functionally equivalent to Thr590 in SEQ ID NO:8 or 12 is a mutation to a non-polar or hydrophobic amino acid, for example Ile.

In other embodiments, an altered polymerase described herein can further include one or more additional substitution mutations selected from a position functionally equivalent to Ala281, Phe283, Thr349, Trp397, or Gly633 in a reference polymerase, such as SEQ ID NO:12.

In one embodiment, an altered polymerase includes a substitution mutation at a position functionally equivalent to Ala281 in a reference polymerase, such as SEQ ID NO:12. In one embodiment, the substitution mutation at a position functionally equivalent to Ala281 is a mutation to a non-polar, hydrophobic, or uncharged amino acid, for example Gly or Phe.

In one embodiment, an altered polymerase includes a substitution mutation at a position functionally equivalent to Phe283 in a reference polymerase, such as SEQ ID NO:12. In one embodiment, the substitution mutation at a position functionally equivalent to Phe283 is a mutation to a polar or uncharged amino acid, for example Ser.

In one embodiment, an altered polymerase includes a substitution mutation at a position functionally equivalent to Trp397 in a reference polymerase, such as SEQ ID NO:12. In one embodiment, the substitution mutation at a position functionally equivalent to Trp397 is a mutation to a polar or uncharged amino acid, for example Cys. In one embodiment, the substitution mutation at a position functionally equivalent to Trp397 is a mutation to a non-polar or hydrophobic amino acid, for example Phe.

In one embodiment, an altered polymerase includes a substitution mutation at a position functionally equivalent to Gly633 in a reference polymerase, such as SEQ ID NO:12. In one embodiment, the substitution mutation at a position functionally equivalent to Gly633 is a mutation to a polar or uncharged amino acid, for example Thr.

In one embodiment, an altered polymerase of the present disclosure includes at least one, at least two, at least three, or at least four, or at least five substitution mutations at a position functionally equivalent to Ala281, Phe283, Trp397, or Gly633 in a reference polymerase such as SEQ ID NO:12.

In other embodiments, an altered polymerase described herein can further include at least one, at least two, or at least three additional substitution mutations chosen from a position functionally equivalent to Tyr291, Gly427, and Asp540 in a reference polymerase, such as SEQ ID NO:8 or 12.

In one embodiment, an altered polymerase includes a substitution mutation at a position functionally equivalent to Tyr291 in a reference polymerase, such as SEQ ID NO:8 or 12. In one embodiment, the substitution mutation at a position functionally equivalent to Tyr291 is a mutation to a polar or uncharged amino acid, for example Cys.

In one embodiment, an altered polymerase includes a substitution mutation at a position functionally equivalent to Gly427 in a reference polymerase, such as SEQ ID NO:8 or 12. In one embodiment, the substitution mutation at a position functionally equivalent to Gly427 is a mutation to a polar amino acid, for example Glu.

In one embodiment, an altered polymerase includes a substitution mutation at a position functionally equivalent to Asp540 in a reference polymerase, such as SEQ ID NO:8 or 12. In one embodiment, the substitution mutation at a position functionally equivalent to Asp540 is a mutation to a polar amino acid, for example Glu.

Modified Nucleotides

The altered polymerases described herein preferentially incorporate the modified nucleotides over degraded nucleotides that lack the 3' block, and as a result have the activity of incorporating nucleotides having a blocking group at a faster rate than degraded nucleotides lacking the blocking group. In one embodiment, the selectivity for incorporating the modified nucleotides over degraded nucleotides is at least 2-fold, at least 3-fold, at least 4-fold, at least 5-fold, at least 6-fold, at least 7-fold, at least 8-fold, at least 9-fold, or at least 10-fold. In one embodiment, the rate of incorporating the modified nucleotides over degraded nucleotides is increased at least 2-fold, at least 3-fold, at least 4-fold, at least 5-fold, at least 6-fold, at least 7-fold, at least 8-fold, at least 9-fold, or at least 10-fold. The nucleotides are modified at the 3' sugar hydroxyl and include modifications at the 3' sugar hydroxyl such that the blocking group is larger in size than the naturally occurring 3' hydroxyl group. Blocking groups are known in the art and are typically attached to a nucleotide at the 3'-carbon atom of the deoxyribose sugar (U.S. Pat. Application Publication No. 2016/0002721). Examples of blocking groups include, but are not limited to, 3'-modified 2-deoxyribonucleoside 5'-triphosphates (3'-modified dNTPs) (Metzker et al., 1994, Nucleic Acids Research, 22 (20): 4259-4267), allyl protecting groups (WO 2002/029003), removable 3'-hydroxy protecting groups forming a structure —O—C(R)$_2$N$_3$ covalently attached to the 3'-carbon atom of a nucleotide (U.S. Patent Application Publication No. 2016/0002721), thermally stable blocking groups (WO 2014/139596), and acetal or thiocarbamate 3'-OH blocking groups, such as allyloxymethyl blocking groups (WO 2020/136170). Examples of blocking groups are also described in U.S. Pat. Nos. 7,427,673, and 7,057,026 and International Application Publication No. WO 2014/139596. In one embodiment, the 3'-OH blocking group is a monofluoromethyl substituted azidomethyl protecting group, a C-amido substituted azidomethyl protecting group, or a difluoromethyl substituted azidomethyl protecting group (U.S. Pat. Application Publication No. 2016/0002721 and International Application Publication No. WO 2004/018497).

Modified polynucleotides identified by an altered polymerase described herein can also include a dye, such as a fluorophore, which specifically identifies the incorporated base. In one embodiment, the fluorophore can be attached to the nucleotide base through a cleavable linker. During a cycle of a sequencing reaction the incorporated base is identified, and the linker can then be cleaved, allowing the fluorophore to be removed and ready for the next base to be attached and identified. The cleavage leaves a remaining "scar" or "pendant arm" moiety located on each of the detected nucleobases. Examples of linkers include, but are not limited to, International Application Publication Nos. WO 2004/018493 and WO 2019/012080, and U.S. Pat. No. 10,526,648.

Mutating Polymerases

Various types of mutagenesis are optionally used in the present disclosure, e.g., to modify polymerases to produce variants, e.g., in accordance with altered polymerases as discussed herein, or using random or semi-random mutational approaches. In general, any available mutagenesis procedure can be used for making an altered polymerase. Such mutagenesis procedures optionally include selection of mutant nucleic acids and polypeptides for one or more activity of interest (e.g., reduced pre-phasing when using ambiently stored modified nucleotides). Procedures that can be used include, but are not limited to: site-directed point mutagenesis, random point mutagenesis, in vitro or in vivo homologous recombination (DNA shuffling and combinatorial overlap PCR), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to persons of skill. The starting polymerase for mutation can be any of those noted herein, including available polymerase mutants such as those identified e.g., in U.S. Pat. Nos. 8,460,910 and 8,623,628.

Optionally, mutagenesis can be guided by known information from a naturally occurring polymerase molecule, or of a known altered polymerase (e.g., using an existing mutant polymerase), e.g., sequence, sequence comparisons, physical properties, crystal structure and/or the like as discussed above. However, in another class of embodiments, modification can be essentially random (e.g., as in classical or "family" DNA shuffling, see, e.g., Crameri et al. (1998), Nature 391:288-291, or by error prone mutagenesis, see, e.g., McCullum et al., (2010), Methods Mol Biol., 634:103-109).

Additional information on mutation formats is found in: Sambrook et al., Molecular Cloning—A Laboratory Manual (3rd Ed.), Vol. 1-3, Cold Spring Harbor Laboratory, Cold Spring Harbor, N.Y., 2000 ("Sambrook"); Current Protocols in Molecular Biology, F. M. Ausubel et al., eds., Current Protocols, a joint venture between Greene Publishing Associates, Inc. and John Wiley & Sons, Inc., (supplemented through 2011) ("Ausubel")) and PCR Protocols A Guide to Methods and Applications (Innis et al. eds) Academic Press Inc. San Diego, Calif. (1990) ("Innis"). The following publications and references cited within provide additional detail on mutation formats: Arnold, Protein engineering for unusual environments, Current Opinion in Biotechnology 4:450-455 (1993); Bass et al., Mutant Trp repressors with new DNA-binding specificities, Science 242:240-245 (1988); Bordo and Argos (1991) Suggestions for "Safe" Residue Substitutions in Site-directed Mutagenesis 217:721-729; Botstein & Shortle, Strategies and applications of in vitro mutagenesis, Science 229:1193-1201 (1985); Carter et al., Improved oligonucleotide site-directed mutagenesis using M13 vectors, Nucl. Acids Res. 13: 4431-4443 (1985); Carter, Site-directed mutagenesis, Biochem. J. 237:1-7 (1986); Carter, Improved oligonucleotide-directed mutagenesis using M13 vectors, Methods in Enzymol. 154: 382-403 (1987); Dale et al., Oligonucleotide-directed random mutagenesis using the phosphorothioate method, Methods Mol. Biol. 57:369-374 (1996); Eghtedarzadeh & Henikoff, Use of oligonucleotides to generate large deletions, Nucl. Acids Res. 14: 5115 (1986); Fritz et al., Oligonucleotide-directed construction of mutations: a gapped duplex DNA procedure without enzymatic reactions in vitro, Nucl. Acids Res. 16: 6987-6999 (1988); Grundstrom et al., Oligonucleotide-directed mutagenesis by microscale 'shot-gun' gene synthesis, Nucl. Acids Res. 13: 3305-3316 (1985); Hayes (2002) Combining Computational and Experimental Screening for rapid Optimization of Protein Properties PNAS 99(25) 15926-15931; Kunkel, The efficiency of oligonucleotide directed mutagenesis, in Nucleic Acids & Molecular Biology (Eckstein, F. and Lilley, D. M. J. eds., Springer Verlag, Berlin)) (1987); Kunkel, Rapid and efficient site-specific mutagenesis without phenotypic selection, Proc. Natl. Acad. Sci. USA 82:488-492 (1985); Kunkel et al., Rapid and efficient site-specific mutagenesis without phenotypic selection, Methods in Enzymol. 154, 367-382 (1987); Kramer et al., The gapped duplex DNA approach to oligonucleotide-directed mutation construction, Nucl. Acids Res. 12: 9441-9456 (1984); Kramer & Fritz Oligonucleotide-directed construction of mutations via gapped duplex DNA, Methods in Enzymol. 154:350-367 (1987); Kramer et al., Point Mismatch Repair, Cell 38:879-887 (1984); Kramer et al., Improved enzymatic in vitro reactions in the gapped duplex DNA approach to oligonucleotide-directed construction of mutations, Nucl. Acids Res. 16: 7207 (1988); Ling et al., Approaches to DNA mutagenesis: an overview, Anal Biochem. 254(2): 157-178 (1997); Lorimer and Pastan Nucleic Acids Res. 23, 3067-8 (1995); Mandecki, Oligonucleotide-directed double-strand break repair in plasmids of *Escherichia coli*: a method for site-specific mutagenesis, Proc. Natl. Acad. Sci. USA, 83:7177-7181(1986); Nakamaye & Eckstein, Inhibition of restriction endonuclease Nci I cleavage by phosphorothioate groups and its application to oligonucleotide-directed mutagenesis, Nucl. Acids Res. 14: 9679-9698 (1986); Nambiar et al., Total synthesis and cloning of a gene coding for the ribonuclease S protein, Science 223: 1299-1301(1984); Sakamar and Khorana, Total synthesis and expression of a gene for the α-subunit of bovine rod outer segment guanine nucleotide-binding protein (transducin), Nucl. Acids Res. 14: 6361-6372 (1988); Sayers et al., Y-T Exonucleases in phosphorothioate-based oligonucleotide-directed mutagenesis, Nucl. Acids Res. 16:791-802 (1988); Sayers et al., Strand specific cleavage of phosphorothioate-containing DNA by reaction with restriction endonucleases in the presence of ethidium bromide, (1988) Nucl. Acids Res. 16: 803-814; Sieber, et al., Nature Biotechnology, 19:456-460 (2001); Smith, In vitro mutagenesis, Ann. Rev. Genet. 19:423-462 (1985); Methods in Enzymol. 100: 468-500 (1983); Methods in Enzymol. 154: 329-350 (1987); Stemmer, Nature 370, 389-91(1994); Taylor et al., The use of phosphorothioate-modified DNA in restriction enzyme reactions to prepare nicked DNA, Nucl. Acids Res. 13: 8749-8764 (1985); Taylor et al., The rapid generation of oligonucleotide-directed mutations at high frequency using phosphorothioate-modified DNA, Nucl. Acids Res. 13: 8765-8787 (1985); Wells et al., Importance of hydrogen-bond formation in stabilizing the transition state of subtilisin, Phil. Trans. R. Soc. Lond. A 317: 415-423 (1986); Wells et al., Cassette mutagenesis: an efficient method for generation of multiple mutations at defined sites, Gene 34:315-323 (1985); Zoller & Smith, Oligonucleotide-directed mutagenesis using M 13-derived vectors: an efficient and general procedure for the production of point mutations in any DNA fragment, Nucleic Acids Res. 10:6487-6500 (1982); Zoller & Smith, Oligonucleotide-directed mutagenesis of DNA fragments cloned into M13 vectors, Methods in Enzymol. 100:468-500 (1983); Zoller & Smith, Oligonucleotide-directed mutagenesis: a simple method using two oligonucleotide primers and a single-stranded DNA template, Methods in Enzymol. 154:329-350 (1987); Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296. Additional details on many of the above methods can be found in Methods in Enzymology Volume 154, which also describes useful controls for trouble-shooting problems with various mutagenesis methods.

Making and Isolating Recombinant Polymerases

Generally, nucleic acids encoding a polymerase as presented herein can be made by cloning, recombination, in vitro synthesis, in vitro amplification and/or other available methods. A variety of recombinant methods can be used for expressing an expression vector that encodes a polymerase as presented herein. Methods for making recombinant nucleic acids, expression and isolation of expressed products are well known and described in the art. A number of exemplary mutations and combinations of mutations, as well as strategies for design of desirable mutations, are described herein. Methods for making and selecting mutations in the active site of polymerases, including for modifying steric features in or near the active site to permit improved access by nucleotide analogs are found herein and, e.g., in International Application Nos. WO 2007/076057 and WO 2008/051530.

Additional useful references for mutation, recombinant and in vitro nucleic acid manipulation methods (including cloning, expression, PCR, and the like) include Berger and Kimmel, Guide to Molecular Cloning Techniques, Methods in Enzymology volume 152 Academic Press, Inc., San Diego, Calif. (Berger); Kaufman et al. (2003) Handbook of Molecular and Cellular Methods in Biology and Medicine Second Edition Ceske (ed) CRC Press (Kaufman); The Nucleic Acid Protocols Handbook Ralph Rapley (ed) (2000) Cold Spring Harbor, Humana Press Inc (Rapley); Chen et al. (ed) PCR Cloning Protocols, Second Edition (Methods in Molecular Biology, volume 192) Humana Press; and in Viljoen et al. (2005) Molecular Diagnostic PCR Handbook Springer, ISBN 1402034032.

In addition, a plethora of kits are commercially available for the purification of plasmids or other relevant nucleic acids from cells, (see, e.g., EasyPrep™ and FlexiPrep™, both from Pharmacia Biotech; StrataClean™, from Stratagene; and QIAprep™ from Qiagen). Any isolated and/or purified nucleic acid can be further manipulated to produce other nucleic acids, incorporated into related vectors to transform cells for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both.

Other useful references, e.g. for cell isolation and culture (e.g., for subsequent nucleic acid isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York); and Atlas and Parks (eds) The Handbook of Microbiological Media (1993) CRC Press, Boca Raton, Fla. Construction of vectors containing a nucleic acid encoding an altered polymerase described herein employs standard ligation techniques known in the art. See, e.g., Sambrook et al, *Molecular Cloning: A Laboratory Manual.*, Cold Spring Harbor Laboratory Press (1989) or Ausubel, R. M., ed. *Current Protocols in Molecular Biology* (1994).

The present disclosure also includes nucleic acids encoding the altered polymerases disclosed herein. A particular amino acid can be encoded by multiple codons, and certain translation systems (e.g., prokaryotic or eukaryotic cells) often exhibit codon bias, e.g., different organisms often prefer one of the several synonymous codons that encode the same amino acid. As such, nucleic acids presented herein are optionally "codon optimized," meaning that the nucleic acids are synthesized to include codons that are preferred by the particular translation system being employed to express the polymerase. For example, when it is desirable to express the polymerase in a bacterial cell (or even a particular strain of bacteria), the nucleic acid can be synthesized to include codons most frequently found in the genome of that bacterial cell, for efficient expression of the polymerase. A similar strategy can be employed when it is desirable to express the polymerase in a eukaryotic cell, e.g., the nucleic acid can include codons preferred by that eukaryotic cell.

A variety of protein isolation and detection methods are known and can be used to isolate polymerases, e.g., from recombinant cultures of cells expressing the recombinant polymerases presented herein. A variety of protein isolation and detection methods are well known in the art, including, e.g., those set forth in R. Scopes, Protein Purification, Springer-Verlag, N.Y. (1982); Deutscher, Methods in Enzymology Vol. 182: Guide to Protein Purification, Academic Press, Inc. N.Y. (1990); Sandana (1997) Bioseparation of Proteins, Academic Press, Inc.; Bollag et al. (1996) Protein Methods, 2nd Edition Wiley-Liss, NY; Walker (1996) The Protein Protocols Handbook Humana Press, NJ, Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice 3rd Edition Springer Verlag, NY; Janson and Ryden (1998) Protein Purification: Principles, High Resolution Methods and Applications, Second Edition Wiley-VCH, NY; and Walker (1998) Protein Protocols on CD-ROM Humana Press, NJ; and the references cited therein. Additional details regarding protein purification and detection methods can be found in Satinder Ahuja ed., Handbook of Bioseparations, Academic Press (2000).

Methods of Use

The altered polymerases presented herein can be used in a sequencing procedure, such as a sequencing-by-synthesis (SBS) technique. Briefly, SBS can be initiated by contacting the target nucleic acids with a mixture of one or more nucleotides, DNA polymerase, etc. Those features where a primer is extended using the target nucleic acid as template will incorporate a labeled nucleotide that can be detected. The labeled nucleotides will typically include a reversible terminator moiety, e.g., a 3' block, that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems, and detection platforms that can be readily adapted for use with an array produced by the methods of the present disclosure are described, for example, in Bentley et al., Nature 456:53-59 (2008); WO 04/018497; WO 91/06678; WO 07/123744; U.S. Pat. Nos. 7,057,026, 7,329,492, 7,211,414, 7,315,019, 7,405,281, and 8,343,746. The pre-phasing typically observed when using ambiently stored modified nucleotides can be significantly reduced using the altered polymerases described herein.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210,891; 6,258,568 and 6,274,320). In pyrosequencing, released PPi can be detected by being converted to adenosine triphosphate (ATP) by ATP sulfurylase, and the resulting ATP can be detected via luciferase-produced photons. Thus, the sequencing reaction can be monitored via a luminescence detection system. Excitation radiation sources used for fluorescence-based detection systems are not necessary for pyrosequencing procedures. Useful fluidic systems, detectors and procedures that can be used for application of pyrosequencing to arrays of the present disclosure are described, for example, in International Application WO 2012/058096, U.S. Pat. Application Pub. No. 2005/0191698 A1, and U.S. Pat. Nos. 7,595,883 and 7,244,559.

Some embodiments can use methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides. Techniques and reagents for FRET-based sequencing are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008).

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in U.S. Pat. Nos. 8,262,900, 7,948,015, 8,349,167, and U.S. Published Patent Application No. 2010/0137143 A1.

Accordingly, presented herein are methods for incorporating nucleotide analogues into DNA including allowing the following components to interact: (i) an altered polymerase according to any of the above embodiments, (ii) a DNA template; and (iii) a nucleotide solution. In certain embodiments, the DNA template includes a clustered array. In certain embodiments, the nucleotides are modified at the 3' sugar hydroxyl, and include modifications at the 3' sugar hydroxyl such that the blocking group is larger in size than the naturally occurring 3' hydroxyl group.

Nucleic Acids Encoding Altered Polymerases

The present disclosure also includes nucleic acid molecules encoding the altered polymerases described herein. For any given altered polymerase which is a mutant version of a polymerase for which the amino acid sequence and, in some embodiments, also the wild type nucleotide sequence encoding the polymerase is known, it is possible to obtain a nucleotide sequence encoding the mutant according to the basic principles of molecular biology. For example, given that the wild type nucleotide sequence encoding 9°N polymerase (SEQ ID NO:1) is known, it is possible to deduce a nucleotide sequence encoding any given mutant version of 9°N having one or more amino acid substitutions using the standard genetic code. Similarly, nucleotide sequences can readily be derived for mutant versions other polymerases such as, for example, Vent® polymerase, Deep Vent® polymerase, Pfu polymerase, KOD polymerase, Pab polymerase, etc. Nucleic acid molecules having the required nucleotide sequence may then be constructed using standard molecular biology techniques known in the art.

In accordance with the embodiments presented herein, a defined nucleic acid includes not only the identical nucleic acid but also any minor base variations including, in particular, substitutions in cases which result in a synonymous codon (a different codon specifying the same amino acid residue) due to the degenerate code in conservative amino acid substitutions. The term "nucleic acid sequence" also includes the complementary sequence to any single stranded sequence given regarding base variations.

The nucleic acid molecules described herein may also, advantageously, be included in a suitable expression vector to express the polymerase proteins encoded therefrom in a suitable host. Incorporation of cloned DNA into a suitable expression vector for subsequent transformation of said cell and subsequent selection of the transformed cells is well known to those skilled in the art as provided in Sambrook et al. (1989), Molecular cloning: A Laboratory Manual, Cold Spring Harbor Laboratory.

Such an expression vector includes a vector having a nucleic acid according to the embodiments presented herein operably linked to regulatory sequences, such as promoter regions, that are capable of effecting expression of said DNA fragments. The term "operably linked" refers to a juxtaposition wherein the components described are in a relationship permitting them to function in their intended manner. Such vectors may be transformed into a suitable host cell to provide for the expression of a protein according to the embodiments presented herein. Suitable hosts include eukaryotic and prokaryotic cells. In one embodiment, a host cell is *E. coli*. Alternatively, vectors may be used in in vitro systems for expression of the polymerase.

The nucleic acid molecule may encode a mature protein or a protein having a pro-sequence, including that encoding a leader sequence on the preprotein which is then cleaved by the host cell to form a mature protein. The vectors may be, for example, plasmid, virus, or phage vectors provided with an origin of replication, and optionally a promoter for the expression of said nucleotide and optionally a regulator of the promoter. A vector may contain one or more selectable markers, such as, for example, an antibiotic resistance gene.

Regulatory elements required for expression include promoter sequences to bind RNA polymerase and to direct an appropriate level of transcription initiation and also translation initiation sequences for ribosome binding. For example, a bacterial expression vector may include a promoter such as the lac promoter and for translation initiation the Shine-Dalgarno sequence and the start codon AUG. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or be assembled from the sequences described by methods well known in the art.

Transcription of DNA encoding the polymerase by higher eukaryotes may be optimized by including an enhancer sequence in the vector. Enhancers are cis-acting elements of DNA that act on a promoter to increase the level of transcription. Vectors will also generally include origins of replication in addition to the selectable markers.

The present disclosure also provides a kit for performing a nucleotide incorporation reaction. The kit includes at least one altered polymerase described herein and a nucleotide solution in a suitable packaging material in an amount sufficient for at least one nucleotide incorporation reaction. Optionally, other reagents such as buffers and solutions needed to use the altered polymerase and nucleotide solution are also included. Instructions for use of the packaged components are also typically included.

In certain embodiments, the nucleotide solution includes labelled nucleotides. In certain embodiments, the nucleotides are synthetic nucleotides. In certain embodiments, the nucleotides are modified nucleotides. In certain embodiments, a modified nucleotide has been modified at the 3' sugar hydroxyl such that the substituent is larger in size than the naturally occurring 3' hydroxyl group. In certain embodiments, the modified nucleotides include a modified nucleotide or nucleoside molecule that includes a purine or pyrimidine base and a ribose or deoxyribose sugar moiety having a removable 3'-OH blocking group covalently attached thereto, such that the 3' carbon atom has attached a group of the structure

—O—Z wherein Z is any of —C(R')$_2$—O—R", —C(R')$_2$—N(R")$_2$, —C(R')$_2$—N(H)R", —C(R')$_2$—S—R" and —C(R')$_2$—F, wherein each R" is or is part of a removable protecting group;

each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; or (R')$_2$ represents an alkylidene group of formula =C(R''')$_2$ wherein each R''' may be the same or different and is selected from the group comprising hydrogen and halogen atoms and alkyl groups; and wherein the molecule may be reacted to yield an intermediate in which each R" is exchanged for H or, where Z is —C(R')$_2$—F, the F is exchanged for OH, SH or NH$_2$, preferably OH, which intermediate dissociates under aqueous conditions to afford a molecule with a free 3'OH;

with the proviso that where Z is —C(R')$_2$—S—R", both R' groups are not H.

In certain embodiments, R' of the modified nucleotide or nucleoside is an alkyl or substituted alkyl. In certain embodiments, —Z of the modified nucleotide or nucleoside is of formula —C(R')$_2$—N$_3$. In certain embodiments, Z is an azidomethyl group.

In certain embodiments, the modified nucleotides are fluorescently labelled to allow their detection. In certain embodiments, the modified nucleotides include a nucleotide or nucleoside having a base attached to a detectable label via a cleavable linker. In certain embodiments, the detectable label includes a fluorescent label.

As used herein, the phrase "packaging material" refers to one or more physical structures used to house the contents of the kit. The packaging material is constructed by known methods, preferably to provide a sterile, contaminant-free environment. The packaging material has a label which indicates that the components can be used for conducting a nucleotide incorporation reaction. In addition, the packaging material contains instructions indicating how the materials within the kit are employed to practice a nucleotide incorporation reaction. As used herein, the term "package" refers to a solid matrix or material such as glass, plastic, paper, foil, and the like, capable of holding within fixed limits the polypeptides. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

The invention is defined in the claims. However, below there is provided a non-exhaustive listing of non-limiting exemplary aspects. Any one or more of the features of these aspects may be combined with any one or more features of another example, embodiment, or aspect described herein.

Exemplary Aspects

Aspect 1 is a recombinant DNA polymerase comprising an amino acid sequence that is at least 80% identical to a DNA polymerase amino acid sequence SEQ ID NO:8 or 12, wherein the recombinant DNA polymerase comprises at least one, at least two, or at least three amino acid substitution mutations at positions functionally equivalent to an amino acid selected from Ala408, Ala409, and Ile410 in the DNA polymerase amino acid sequence.

Aspect 2 is the recombinant DNA polymerase of Aspect 1, wherein the substitution mutation at the position functionally equivalent to Ala408 comprises a mutation to a polar or uncharged amino acid.

Aspect 3 is the recombinant DNA polymerase of any one of Aspects 1-2, wherein the substitution mutation at the position functionally equivalent to Ala408 comprises a mutation to Tyr.

Aspect 4 is the recombinant DNA polymerase of any one of Aspects 1-3, wherein the substitution mutation at the position functionally equivalent to Ala409 comprises a mutation to a non-polar or hydrophobic amino acid.

Aspect 5 is the recombinant DNA polymerase of any one of Aspects 1-4, wherein the substitution mutation at the position functionally equivalent to Ala409 comprises a mutation to Pro.

Aspect 6 is the recombinant DNA polymerase of any one of Aspects 1-5, wherein the substitution mutation at the position functionally equivalent to Ile410 comprises a mutation to a non-polar or hydrophobic amino acid.

Aspect 7 is the recombinant DNA polymerase of any one of Aspects 1-6, wherein the substitution mutation at the position functionally equivalent to Ile410 comprises a mutation to Ala or Pro.

Aspect 8 is a recombinant DNA polymerase comprising an amino acid sequence that is at least 80% identical to a DNA polymerase amino acid sequence SEQ ID NO:8 or 12, wherein the recombinant DNA polymerase comprises at least one, at least two, or at least three amino acid substitution mutations at positions functionally equivalent to an amino acid selected from Ala408, Ala409, and Ile410 in the DNA polymerase amino acid sequence, and further comprising at least one, at least two, at least three, at least four, at least five, at least six, at least seven, at least eight, or at least nine amino acid substitution mutations at positions functionally equivalent to an amino acid selected from Ala129, Ala141, Ala143, Ser223, Val485, Gly497, Tyr247, Asp599, and Gly633 in the DNA polymerase amino acid sequence.

Aspect 9 is the recombinant DNA polymerase of Aspect 8, wherein the substitution mutation at the position functionally equivalent to Ala129 comprises a mutation to any amino acid other than Met.

Aspect 10 is the recombinant DNA polymerase of any one of Aspects 8-9, wherein the substitution mutation at the position functionally equivalent to Ala 141 comprises a mutation to a non-polar or hydrophobic amino acid.

Aspect 11 is the recombinant DNA polymerase of any one of Aspects 8-10, wherein the substitution mutation at the position functionally equivalent to Ala 143 comprises a mutation to a non-polar or hydrophobic amino acid.

Aspect 12 is the recombinant DNA polymerase of any one of Aspects 8-11, wherein the substitution mutation at the position functionally equivalent to Ser223 comprises a mutation to a polar or uncharged amino acid.

Aspect 13 is the recombinant DNA polymerase of any one of Aspects 8-12, wherein the substitution mutation at the position functionally equivalent to Val485 comprises a mutation to a non-polar or hydrophobic amino acid.

Aspect 14 is the recombinant DNA polymerase of any one of Aspects 8-13, wherein the substitution mutation at the position functionally equivalent to Gly497 comprises a mutation to a non-polar, hydrophobic, or uncharged amino acid.

Aspect 15 is the recombinant DNA polymerase of any one of Aspects 8-14, wherein the substitution mutation at the position functionally equivalent to Tyr247 comprises a mutation to a polar or uncharged amino acid.

Aspect 16 is the recombinant DNA polymerase of any one of Aspects 8-15, wherein the substitution mutation at the position functionally equivalent to Asp599 comprises a mutation to a polar amino acid.

Aspect 17 is the recombinant DNA polymerase of any one of Aspects 8-16, wherein the substitution mutation at the position functionally equivalent to Gly633 comprises a mutation to a non-polar, hydrophobic, or uncharged amino acid.

Aspect 18 is the recombinant DNA polymerase of any one of Aspects 1-17, wherein the DNA polymerase is SEQ ID NO:12, and wherein the DNA polymerase further comprises an amino acid substitution mutation at a position functionally equivalent to Lys349, wherein the substitution mutation is to Ser or Asn.

Aspect 19 is the recombinant DNA polymerase of any one of Aspects 1-18, wherein the polymerase further comprises at least one or at least two amino acid substitution mutations at positions functionally equivalent to an amino acid selected from Lys620 and Val661 in the DNA polymerase amino acid sequence SEQ ID NO:8 or 12, wherein the substitution mutation at Lys620 is to Arg, and wherein the substitution mutation at Val661 is to Asp.

Aspect 20 is the recombinant DNA polymerase of any one of Aspects 1-19, wherein the polymerase further comprises at least one, at least two, at least three, or at least four amino acid substitution mutations at positions functionally equivalent to an amino acid selected from Ala281, Phe283, Trp397, and Gly633 in the DNA polymerase amino acid sequence SEQ ID NO: 12, wherein the substitution mutation at Ala281 is to Phe, wherein the substitution mutation at Phe283 is to Ser, wherein the substitution mutation at Trp397 is to Cys, and wherein the substitution mutation at Gly663 is to Thr.

Aspect 21. A recombinant polymerase comprising the amino acid sequence chosen from SEQ ID NOs:9, 10, 11, 13, 14, 15, 16, 17, and 18, where the substitution mutation at the position functionally equivalent to Ala408 comprises a mutation to a polar or uncharged amino acid, such as Tyr, where the substitution mutation at the position functionally equivalent to Ala409 comprises a mutation to a non-polar or hydrophobic amino acid, such as Pro, and where the substitution mutation at the position functionally equivalent to Ile410 comprises a mutation to a non-polar or hydrophobic amino acid, such as Ala or Pro.

Aspect 22 is the recombinant DNA polymerase of any one of Aspects 1-20, wherein the recombinant polymerase is a family B type DNA polymerase.

Aspect 23 is the recombinant DNA polymerase of Aspect 22, wherein the family B type DNA polymerase is selected from a family B archaeal DNA polymerase, a human DNA polymerase-a, T4 polymerase, RB69 polymerase, and phi29 phage DNA polymerase. \

Aspect 24 is the recombinant DNA polymerase of Aspect 22 or 23, wherein the family B archaeal DNA polymerase is from a genus selected from *Thermococcus, Pyrococcus, Pyrobaculum, Pyrodictium, Aeropyrum* and *Methanococcus*.

Aspect 25 is the recombinant DNA polymerase of any of Aspects 1-24, wherein the polymerase comprises reduced exonuclease activity as compared to a wild type polymerase.

Aspect 26 is a nucleic acid molecule encoding a recombinant DNA polymerase as defined in any one of Aspects 1-25.

Aspect 27 is an expression vector comprising the nucleic acid molecule of Aspect 26.

Aspect 28 is a host cell comprising the vector of Aspect 27.

Aspect 29 is a method for incorporating modified nucleotides into DNA comprising allowing the following components to interact: (i) a recombinant DNA polymerase according to any one of Aspects 1-25, (ii) a DNA template; and (iii) a nucleotide solution.

Aspect 30 is the method of Aspect 29, wherein the DNA template comprises a clustered array.

Aspect 31 is a kit for performing a nucleotide incorporation reaction comprising: a recombinant DNA polymerase as defined in any one of Aspects 1-25 and a solution comprising modified nucleotides.

Aspect 32 is the kit of Aspect 31, wherein the modified nucleotides comprise a detectable label.

Aspect 33 is the kit of Aspect 31 or 32, wherein the modified nucleotides have been modified at the 3' sugar hydroxyl such that the substituent is larger in size than the naturally occurring 3' hydroxyl group.

Aspect 34 is the kit of any one of Aspects 31-33, wherein the modified nucleotides comprise a modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure

—O—Z wherein Z is any of —C(R')$_2$—O—R", —C(R')$_2$—N(R")$_2$, —C(R')$_2$—N(H)R", —C(R')$_2$—S—R" and —C(R')$_2$—F, wherein each R" is or is part of a removable protecting group;

each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; or (R')$_2$ represents an alkylidene group of formula =C(R''')$_2$ wherein each R''' may be the same or different and is selected from the group comprising hydrogen and halogen atoms and alkyl groups; and wherein said molecule may be reacted to yield an intermediate in which each R" is exchanged for H or, where Z is —C(R')$_2$—F, the F is exchanged for OH, SH or NH$_2$, preferably OH, which intermediate dissociates under aqueous conditions to afford a molecule with a free 3'OH;

with the proviso that where Z is —C(R')$_2$—S—R", both R' groups are not H.

Aspect 35 is the kit of Aspect 34, wherein R' of the modified nucleotide or nucleoside is an alkyl or substituted alkyl.

Aspect 36 is the kit of any one of Aspects 31-35, wherein Z of the modified nucleotide or nucleoside is of formula —C(R')$_2$—N$_3$.

Aspect 37 is the kit of any one of Aspects 31-36, wherein Z is an azidomethyl group.

Aspect 38 is the kit of any one of Aspects 31-37, wherein the modified nucleotides comprise a nucleotide or nucleoside having a base attached to a detectable label via a cleavable linker.

Aspect 39 is the kit of any one of Aspects 31-38, wherein the detectable label comprises a fluorescent label.

Aspect 40 is the kit of any one of Aspects 31-39, further comprising one or more DNA template molecules and/or primers.

EXAMPLES

The present disclosure is illustrated by the following examples. It is to be understood that the particular examples, materials, amounts, and procedures are to be interpreted broadly in accordance with the scope and spirit of the disclosure as set forth herein.

Example 1

General Assay Methods and Conditions

Unless otherwise noted, this describes the general assay conditions used in the Examples described herein.
A. Cloning and Expression of Polymerases Methods for making recombinant nucleic acids, expression, and isolation of expressed products are known and described in the art. Mutagenesis was performed on the coding region encoding a 9°N polymerase (SEQ ID NO:1) using standard site-directed mutagenesis methodology. For each mutation made, the proper sequence of the altered coding region was confirmed by determining the sequence of the cloned DNA.

His-tagged mutant polymerase coding regions were subcloned into pET11a vector and transformed into Acella expression cells (Edge Bio, San Jose, CA). Freezer stocks from single-picked colonies were used to inoculate overnight expression cultures in 2.8 L flasks. Cultures were grown at 37° C. until OD600 of about 0.9-1.0, protein expression was then induced with 0.2 mM IPTG and followed by 4 hours of additional growth. Cultures were centrifuged at 5,000×g for 20 minutes. Cell pellets were stored at −20° C. until purification.

Pellets were freeze-thawed and lysed with 5×w/v lysis buffer (50 mM Tris-HCl pH7.5, 1 mM EDTA, 0.1% v/v BME, and 5% Glycerol) in the presence of Ready-Lyse and Omnicleave reagents (Epicentre. Madison, WI) according to manufacturer recommendations. The final NaCl concentration was raised to 500 mM and lysate was incubated on ice for 5 minutes. Following centrifugation, the supernatant was incubated at 80° C. for about 70 minutes. All further purification was performed at 4° C. Supernatant was iced for 30 min before being centrifuged and purified using 3 mL HisPur Ni-NTA Spin columns (Thermo-Fisher). Columns were pre-equilibrated with HIS Buffer A (50 mM Tris-HCl pH 7.5, 5% Glycerol, 500 mM NaCl, and 10 mM Imidazole). The column was eluted by using 3×3 mL of HIS Buffer B (50 mM Tris-HCl pH 7.5, 5% Glycerol, 500 mM NaCl, and 500 mM Imidazole). Eluted fractions were combined and diluted with Modified SP Buffer A (50 mM Tris-HCl pH 7.5, 1 mM EDTA, 5% Glycerol) to match the conductivity of SP Buffer A (50 mM Tris-HCl pH 7.5, 150 mM NaCl, 1 mM EDTA, 5% Glycerol) and loaded onto 5 mL SP Sepharose columns (GE). The column was eluted using a 100 mL gradient from 150 to 1000 mM NaCl. Peak fractions were pooled, buffer exchanged using 15 mL 10 kDa Spin Filter columns (Millipore) into 2× storage buffer (20 mM Tris-HCl pH 7.5, 600 mM KCl, 0.2 mM EDTA), then diluted 2× with 100% Glycerol to create the final 1× storage buffer (10 mM Tris-HCl pH 7.5, 300 mM KCl, 0.1 mM EDTA, 50% Glycerol). Samples were then stored at −20° C.

B. Error Rate and Phasing Analysis

Sequencing experiments were used to compare error rates, phasing values and pre-phasing values. Unless indicated otherwise, the experiments were carried out on a MiniSeq™ system (Illumina, Inc., San Diego, Calif.), according to manufacturer instructions. For example, for each polymerase, a separate incorporation mix (IMX) was prepared and used in a short run (61 cycles in read 1) or long run (151 cycle run in read 1 and 151 cycle run in read 2). In case of 61 cycle runs, the first 25 cycles used standard cartridge formulation to establish baseline and remaining 36 cycles used custom formulations containing altered polymerase and varying dNTP:ffN ratios. Standard MiniSeq Mid Output Reagent Cartridge formulations were used, with the standard polymerase substituted with the polymerase being tested, at a concentration of 90 µg/mL. The time for incubation of IMX and ratio of dNTP:ffN in the IMX on the flowcell varied as noted in the Examples herein. To assess pre-phasing performance improvements, varying amounts of Deoxynucleotides (dNTP) (New England Biotech) were titrated into the Standard MiniSeq Mid Output Reagent Cartridge formulations to yield custom formulations with 0-10% dNTP:ffN ratios, along with the substituted polymerases to challenge the polymerase.

The DNA library used was made following the standard TruSeq™ Nano protocol (Illumina, Inc.), with 350 bp target insert size, using *E. coli* genomic DNA; PhiX DNA (Illumina, Inc) was added to resulting library in ~1:10 molar ratio. Illumina RTA Software was used to evaluate error rate on both genomes as well as pre-phasing and phasing levels.

Example 2

Sequencing Performance of Selected Altered Polymerases with Improved Pre-Phasing Metrics Several altered polymerases were identified that had low pre-phasing levels in a short run under a longer incorporation time (e.g., 92 sec) compared to a control polymerase (Pol A) used in a longer run with standard incorporation mix (92 sec). The quality metrics used to evaluate the altered polymerases were the pre-phasing rates ("PrePhasing Weight"), phasing rates ("Phasing Weight") and cumulative error rates of *E. coli* and bacteriophage PhiX sequencing controls ("Error Rate"). Results are summarized in FIG. 2 and include examples of three polymerases (Pol B, Pol C, and Pol D) with improved pre-phasing of which two enzymes further exhibit good phasing and error rates in addition to lower pre-phasing (Pol B and Pol C).

Example 3

Superior Sequencing Performance of Pol B in Presence of dNTPs

Figure 3:
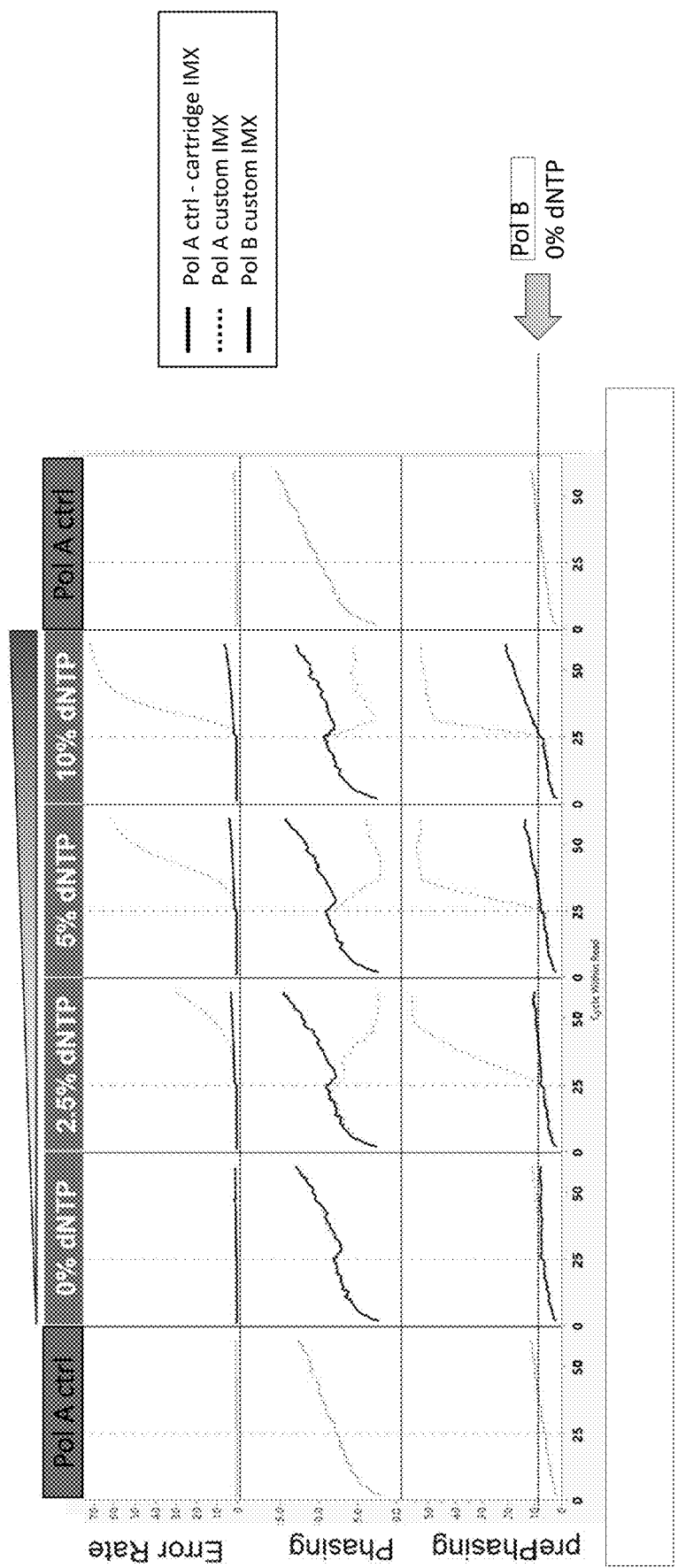
FIG. 3 shows the error rates, phasing levels, and pre-phasing levels of the Pol A and Pol B polymerases. Pol A and Pol B are described in Brief Description of FIG. 2. Columns 1 and 6 show the control under conditions of no added dNTP, and columns 2-5 show the Pol A and Pol B polymerases in incorporation mixes containing 0, 2.5%, 5% and 10% dNTP: ffN. In columns 2-5 the dashed line shows the Pol A polymerase and the solid line shows the Pol B polymerase. "Error Rate," "Phasing," and "prePhasing" refer to error rate, phasing rate, and pre-phasing rates during Read 1.

To compare dNTP sensitivity of control polymerase versus one altered variant, Pol A and Pol B polymerases were tested in incorporation mixes containing 0, 2.5%, 5% and 10% dNTP:ffN. FIG. 3 shows an example where the polymerases exhibit identical performance at 0% dNTP in the incorporation mix, but at increasing % of dNTP Pol B performance degrades much slower than pol Pol A. Pol B had improved resistance to recognizing and incorporating nucleotides with a free 3'OH compared to nucleotides with a blocking group.

Example 4

Improved Pre-Phasing Pol B in 2×151 Runs

Pol B and Pol A were compared in traditional longer runs to test whether the mutations on this mutant could prove advantageous to improved pre-phasing. Pol B can maintain lower pre-phasing through both reads when a longer run of 150 cycles for Read 1 and 150 cycles for Read 2 was used (data not shown).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The disclosure is not limited to the exact details shown and described, for variations obvious to one skilled in the art will be included within the disclosure defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present disclosure. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The invention claimed is:

1. A recombinant family B archaeal DNA polymerase comprising an amino acid sequence that is at least 80% identical to a DNA polymerase amino acid sequence SEQ ID NO:8 or 12, wherein the recombinant DNA polymerase comprises at least two substitution mutations, wherein the first substitution mutation at the position functionally equivalent to Ala408 comprises a mutation to Tyr, and wherein the second substitution mutation at the position functionally equivalent to Ala409 comprises a mutation to Pro, and wherein the recombinant DNA polymerase preferentially incorporates a nucleotide having a blocking group at a faster rate than a nucleotide lacking the blocking group.

2. A recombinant family B archaeal DNA polymerase comprising an amino acid sequence that is at least 80% identical to a DNA polymerase amino acid sequence SEQ ID NO:8 or 12, wherein the recombinant DNA polymerase comprises at least two substitution mutations, wherein the first substitution mutation at the position functionally equivalent to Ala408 comprises a mutation to Tyr, and wherein the second substitution mutation at the position functionally equivalent to Ala409 comprises a mutation to Pro, and further comprising at least one, at least two, at least three, at least four, at least five, at least six, at least seven, at least eight, or at least nine amino acid substitution mutations at positions functionally equivalent to an amino acid selected from Ala129, Ala141, Ala143, Ser223, Val485, Gly497, Tyr247, Asp599, and Gly633 in the DNA polymerase amino acid sequence, and wherein the recombinant DNA polymerase preferentially incorporates a nucleotide having a blocking group at a faster rate than a nucleotide lacking the blocking group.

3. The recombinant family B archaeal DNA polymerase of claim 2, wherein the substitution mutation at the position functionally equivalent to Ala129 comprises a mutation to any amino acid other than Met.

4. The recombinant family B archaeal DNA polymerase of claim 2, wherein the substitution mutation at the position functionally equivalent to Ala 141 comprises a mutation to a non-polar or hydrophobic amino acid.

5. The recombinant family B archaeal DNA polymerase of claim 2, wherein the substitution mutation at the position functionally equivalent to Ala 143 comprises a mutation to a non-polar or hydrophobic amino acid.

6. The recombinant family B archaeal DNA polymerase of claim 2, wherein the substitution mutation at the position functionally equivalent to Ser223 comprises a mutation to a polar or uncharged amino acid.

7. The recombinant family B archaeal DNA polymerase of claim 2, wherein the substitution mutation at the position functionally equivalent to Val485 comprises a mutation to a non-polar or hydrophobic amino acid.

8. The recombinant family B archaeal DNA polymerase of claim 2, wherein the substitution mutation at the position functionally equivalent to Gly497 comprises a mutation to a non-polar, hydrophobic, or uncharged amino acid.

9. The recombinant family B archaeal DNA polymerase of claim 2, wherein the substitution mutation at the position functionally equivalent to Tyr247 comprises a mutation to a polar or uncharged amino acid.

10. The recombinant family B archaeal DNA polymerase of claim 2, wherein the substitution mutation at the position functionally equivalent to Asp599 comprises a mutation to a polar amino acid.

11. The recombinant family B archaeal DNA polymerase of claim 2, wherein the substitution mutation at the position functionally equivalent to Gly633 comprises a mutation to a non-polar, hydrophobic, or uncharged amino acid.

12. The recombinant family B archaeal DNA polymerase of claim 1, wherein the DNA polymerase is SEQ ID NO:12, and wherein the DNA polymerase further comprises an amino acid substitution mutation at a position functionally equivalent to Lys349, wherein the substitution mutation is to Ser or Asn.

13. The recombinant family B archaeal DNA polymerase of claim 1, wherein the DNA polymerase further comprises at least one or at least two amino acid substitution mutations at positions functionally equivalent to an amino acid selected from Lys620 and Val661 in the DNA polymerase amino acid sequence SEQ ID NO:8 or 12, wherein the substitution mutation at Lys620 is to Arg, and wherein the substitution mutation at Val661 is to Asp.

14. The recombinant family B archaeal DNA polymerase of claim 1, wherein the DNA polymerase further comprises at least one, at least two, at least three, or at least four amino acid substitution mutations at positions functionally equivalent to an amino acid selected from Ala281, Phe283, Trp397, and Gly633 in the DNA polymerase amino acid sequence SEQ ID NO: 12, wherein the substitution mutation at Ala281 is to Phe, wherein the substitution mutation at Phe283 is to Ser, wherein the substitution mutation at Trp397 is to Cys, and wherein the substitution mutation at Gly663 is to Thr.

15. A recombinant family B archaeal DNA polymerase comprising the amino acid sequence chosen from SEQ ID NOs:9, 10, 11, 13, 14, 15, 16, 17, and 12, and comprising two substitution mutations, wherein the first substitution mutation at the position functionally equivalent to Ala408 comprises a mutation to a polar or uncharged amino acid, wherein the second substitution mutation at the position functionally equivalent to Ala409 comprises a mutation to a non-polar or hydrophobic amino acid, and wherein the recombinant DNA polymerase preferentially incorporates a nucleotide having a blocking group at a faster rate than a nucleotide lacking the blocking group.

16. The recombinant family B archaeal DNA polymerase of claim 1, wherein the family B archaeal DNA polymerase is from a genus selected from *Thermococcus, Pyrococcus, Pyrobaculum, Pyrodictium, Aeropyrum* and *Methanococcus*.

17. The recombinant family B archaeal DNA polymerase of claim 1, wherein the polymerase comprises reduced exonuclease activity as compared to a wild type polymerase.

18. A method for incorporating modified nucleotides into DNA comprising allowing the following components to interact: (i) a recombinant family B archaeal DNA polymerase according to claim 1, (ii) a DNA template; and (iii) a nucleotide solution.

19. The method of claim 18, wherein the DNA template comprises a clustered array.

20. A kit for performing a nucleotide incorporation reaction comprising: a recombinant family B archaeal DNA polymerase as defined in claim 1 and a solution comprising modified nucleotides.

21. The kit of claim 20, wherein the modified nucleotides comprise a detectable label.

22. The kit of claim 20, wherein the modified nucleotides have been modified at the 3' sugar hydroxyl such that the substituent is larger in size than the naturally occurring 3' hydroxyl group.

23. The kit of claim 22, wherein the modified nucleotides comprise a modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure

—O—Z wherein Z is any of —C(R')$_2$—O—R", —C(R')$_2$—N(R")$_2$, —C(R')$_2$—N(H)R", —C(R')$_2$—S—R" and —C(R')$_2$—F, wherein each R" is or is part of a removable protecting group;

each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; or (R')$_2$ represents an alkylidene group of formula =C(R''')$_2$ wherein each R''' may be the same or different and is selected from the group comprising hydrogen and halogen atoms and alkyl groups; and wherein said molecule may be reacted to yield an intermediate in which each R" is exchanged for H or, where Z is —C(R')$_2$—F, the F is exchanged for OH, SH or NH$_2$, preferably OH, which intermediate dissociates under aqueous conditions to afford a molecule with a free 3'OH;

with the proviso that where Z is —C(R')2-S—R", both R' groups are not H.

24. The kit of claim 23, wherein R' of the modified nucleotide or nucleoside is an alkyl or substituted alkyl.

25. The kit of claim 23, wherein Z of the modified nucleotide or nucleoside is of formula —C(R')$_2$—N$_3$.

26. The kit of claim 25, wherein Z is an azidomethyl group.

27. The kit of claim 20, wherein the modified nucleotides comprise a nucleotide or nucleoside having a base attached to a detectable label via a cleavable linker.

28. The kit of claim 27, wherein the detectable label comprises a fluorescent label.

29. The kit of claim 20, further comprising one or more DNA template molecules and/or primers.

30. The recombinant family B archaeal DNA polymerase of claim 1, wherein the recombinant DNA polymerase further comprises a third substitution mutation, wherein the third substitution mutation is at the position functionally equivalent to Ile410.

31. The recombinant family B archaeal DNA polymerase of claim 30, wherein the substitution mutation at the position functionally equivalent to Ile410 comprises a mutation to a non-polar or hydrophobic amino acid.

32. The recombinant family B archaeal DNA polymerase of claim 31, wherein the substitution mutation at the position functionally equivalent to Ile410 comprises a mutation to Ala or Pro.

33. The recombinant family B archaeal DNA polymerase of claim 15, wherein the recombinant DNA polymerase further comprises a third substitution mutation, wherein the third substitution mutation is at the position functionally equivalent to Ile410, wherein the mutation is to a non-polar or hydrophobic amino acid.

\* \* \* \* \*

SEQUENCE LISTING

```
<160> NUMBER OF SEQ ID NOS: 24

<210> SEQ ID NO 1
<211> LENGTH: 775
<212> TYPE: PRT
<213> ORGANISM: Thermococcus sp.

<400> SEQUENCE: 1

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Asp Ile Glu Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190
```

```
Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
            290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
            370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605
```

```
Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
770                 775

<210> SEQ ID NO 2
<211> LENGTH: 774
<212> TYPE: PRT
<213> ORGANISM: artificial
<220> FEATURE:
<223> OTHER INFORMATION: altered polymerase

<400> SEQUENCE: 2

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
                20                  25                  30

His Phe Gln Pro Tyr Ile Tyr Ala Leu Leu Lys Asp Asp Ser Ala Ile
            35                  40                  45

Glu Glu Ile Lys Ala Ile Lys Gly Glu Arg His Gly Lys Thr Val Arg
50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Ala Ile Ala Thr
130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190
```

```
Arg Phe Val Gln Val Val Lys Glu Lys Asp Pro Asp Val Ile Ile Thr
            195                 200                 205

Tyr Asn Gly Asp Asn Phe Asp Leu Pro Tyr Leu Ile Lys Arg Ala Glu
        210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
        355                 360                 365

Leu Ala Pro Asn Lys Pro Asp Glu Glu Tyr Lys Arg Arg Leu Arg
370                 375                 380

Thr Thr Tyr Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
        435                 440                 445

Pro Gly Phe Ile Pro Ser Ile Leu Gly Asp Leu Ile Ala Met Arg Gln
450                 455                 460

Asp Ile Lys Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                485                 490                 495

Tyr Gly Tyr Met Gly Tyr Pro Lys Ala Arg Trp Tyr Ser Lys Glu Cys
            500                 505                 510

Ala Glu Ser Val Thr Ala Trp Gly Arg His Tyr Ile Glu Met Thr Ile
        515                 520                 525

Arg Glu Ile Glu Glu Lys Phe Gly Phe Lys Val Leu Tyr Ala Asp Thr
530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
595                 600                 605
```

-continued

```
Arg Gly Leu Glu Val Val Arg Arg Asp Trp Ser Glu Ile Ala Lys Glu
    610                 615                 620
Thr Gln Ala Lys Val Leu Glu Ala Ile Leu Lys Glu Gly Ser Val Glu
625                 630                 635                 640
Lys Ala Val Glu Val Val Arg Asp Val Val Glu Lys Ile Ala Lys Tyr
                645                 650                 655
Arg Val Pro Leu Glu Lys Leu Val Ile His Glu Gln Ile Thr Arg Asp
                660                 665                 670
Leu Lys Asp Tyr Lys Ala Ile Gly Pro His Val Ala Ile Ala Lys Arg
            675                 680                 685
Leu Ala Ala Arg Gly Ile Lys Val Lys Pro Gly Thr Ile Ile Ser Tyr
        690                 695                 700
Ile Val Leu Lys Gly Ser Gly Lys Ile Ser Asp Arg Val Ile Leu Leu
705                 710                 715                 720
Thr Glu Tyr Asp Pro Arg Lys His Lys Tyr Asp Pro Asp Tyr Tyr Ile
                725                 730                 735
Glu Asn Gln Val Leu Pro Ala Val Leu Arg Ile Leu Glu Ala Phe Gly
            740                 745                 750
Tyr Arg Lys Glu Asp Leu Arg Tyr Gln Ser Ser Lys Gln Thr Gly Leu
        755                 760                 765
Asp Ala Trp Leu Lys Arg
    770

<210> SEQ ID NO 3
<211> LENGTH: 777
<212> TYPE: PRT
<213> ORGANISM: artificial
<220> FEATURE:
<223> OTHER INFORMATION: altered polymerase

<400> SEQUENCE: 3

Met Ile Leu Asp Ala Asp Tyr Ile Thr Glu Asp Gly Lys Pro Ile Ile
1               5                   10                  15
Arg Ile Phe Lys Lys Glu Asn Gly Glu Phe Lys Val Glu Tyr Asp Arg
                20                  25                  30
Asn Phe Arg Pro Tyr Ile Tyr Ala Leu Leu Lys Asp Asp Ser Gln Ile
            35                  40                  45
Asp Glu Val Arg Lys Ile Thr Ala Glu Arg His Gly Lys Ile Val Arg
        50                  55                  60
Ile Ile Asp Ala Glu Lys Val Arg Lys Lys Phe Leu Gly Arg Pro Ile
65                  70                  75                  80
Glu Val Trp Arg Leu Tyr Phe Glu His Pro Gln Asp Val Pro Ala Ile
                85                  90                  95
Arg Asp Lys Ile Arg Glu His Ser Ala Val Ile Asp Ile Phe Glu Tyr
            100                 105                 110
Asp Ile Pro Phe Ala Lys Arg Tyr Leu Ile Asp Lys Gly Leu Ile Pro
        115                 120                 125
Met Glu Gly Asp Glu Glu Leu Lys Leu Leu Ala Phe Asp Ile Glu Thr
    130                 135                 140
Leu Tyr His Glu Gly Glu Glu Phe Ala Lys Gly Pro Ile Ile Met Ile
145                 150                 155                 160
Ser Tyr Ala Asp Glu Glu Glu Ala Lys Val Ile Thr Trp Lys Lys Ile
                165                 170                 175
Asp Leu Pro Tyr Val Glu Val Val Ser Ser Glu Arg Glu Met Ile Lys
            180                 185                 190
```

```
Arg Phe Leu Lys Val Ile Arg Glu Lys Asp Pro Asp Val Ile Ile Thr
            195                 200                 205

Tyr Asn Gly Asp Ser Phe Asp Leu Pro Tyr Leu Val Lys Arg Ala Glu
        210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
                    260                 265                 270

Tyr Thr Leu Glu Ala Val Tyr Glu Ala Ile Phe Gly Lys Pro Lys Glu
            275                 280                 285

Lys Val Tyr Ala His Glu Ile Ala Glu Ala Trp Glu Thr Gly Lys Gly
        290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
                    340                 345                 350

Val Glu Trp Tyr Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
        370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
                    420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Glu Ile
        450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
                580                 585                 590

Lys Lys Tyr Ala Leu Ile Asp Glu Glu Gly Lys Ile Ile Thr Arg Gly
            595                 600                 605
```

-continued

```
Leu Glu Ile Val Arg Arg Asp Trp Ser Glu Ile Ala Lys Glu Thr Gln
610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
                660                 665                 670

Glu Tyr Lys Ala Ile Gly Pro His Val Ala Val Ala Lys Arg Leu Ala
            675                 680                 685

Ala Arg Gly Val Lys Val Arg Pro Gly Met Val Ile Gly Tyr Ile Val
690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
                740                 745                 750

Lys Glu Asp Leu Arg Trp Gln Lys Thr Lys Gln Thr Gly Leu Thr Ala
            755                 760                 765

Trp Leu Asn Ile Lys Lys Gly Ser
770                 775

<210> SEQ ID NO 4
<211> LENGTH: 775
<212> TYPE: PRT
<213> ORGANISM: artificial
<220> FEATURE:
<223> OTHER INFORMATION: altered polymerase

<400> SEQUENCE: 4

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
                20                  25                  30

Thr Phe Arg Pro Tyr Ile Tyr Ala Leu Leu Arg Asp Asp Ser Lys Ile
            35                  40                  45

Glu Glu Val Lys Lys Ile Thr Gly Glu Arg His Gly Lys Ile Val Arg
        50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Glu Glu Glu Leu Lys Ile Leu Ala Phe Ala Ile Ala Thr
130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
                180                 185                 190
```

```
Arg Phe Leu Arg Ile Ile Arg Glu Lys Asp Pro Asp Ile Val Thr
                195                 200                 205
Tyr Asn Gly Asp Ser Phe Asp Phe Pro Tyr Leu Ala Lys Arg Ala Glu
210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Thr Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Ser Gly Glu Asn
    290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
        355                 360                 365
Pro Asn Lys Pro Ser Glu Glu Tyr Gln Arg Arg Leu Arg Glu Ser
    370                 375                 380
Tyr Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Ile Thr
                405                 410                 415
His Asn Val Ser Pro Asp Thr Leu Asn Leu Glu Gly Cys Lys Asn Tyr
            420                 425                 430
Asp Ile Ala Pro Gln Val Gly His Lys Phe Cys Lys Asp Ile Pro Gly
        435                 440                 445
Phe Ile Pro Ser Leu Leu Gly His Leu Leu Glu Glu Arg Gln Lys Ile
    450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Lys Tyr Ile Glu Leu Val Trp Lys Glu
        515                 520                 525
Leu Glu Glu Lys Phe Gly Phe Lys Val Leu Tyr Ile Asp Thr Asp Gly
    530                 535                 540
Leu Tyr Ala Thr Ile Pro Gly Gly Glu Ser Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Arg Tyr Ala Val Ile Asp Glu Glu Gly Lys Val Ile Thr Arg Gly
        595                 600                 605
```

```
Leu Glu Ile Val Arg Arg Asp Trp Ser Glu Ile Ala Lys Glu Thr Gln
            610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
            755                 760                 765

Trp Leu Asn Ile Lys Lys Ser
    770                 775

<210> SEQ ID NO 5
<211> LENGTH: 774
<212> TYPE: PRT
<213> ORGANISM: artificial
<220> FEATURE:
<223> OTHER INFORMATION: altered polymerase

<400> SEQUENCE: 5

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
                100                 105                 110

Asp Ile Pro Phe Ala Lys Arg Tyr Leu Ile Asp Lys Gly Leu Val Pro
            115                 120                 125

Met Glu Gly Asp Glu Glu Leu Lys Met Leu Ala Phe Ala Ile Ala Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190
```

```
Arg Phe Leu Arg Val Val Lys Glu Lys Asp Pro Asp Val Leu Ile Thr
            195                 200                 205
Tyr Asn Gly Asp Asn Phe Asp Phe Ala Tyr Leu Lys Lys Arg Cys Glu
        210                 215                 220
Lys Leu Gly Ile Asn Phe Ala Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
            260                 265                 270
Tyr Thr Leu Glu Ala Val Tyr Glu Ala Val Phe Gly Gln Pro Lys Glu
        275                 280                 285
Lys Val Tyr Ala Glu Glu Ile Thr Thr Ala Trp Glu Thr Gly Glu Asn
290                 295                 300
Leu Glu Arg Val Ala Arg Tyr Ser Met Glu Asp Ala Lys Val Thr Tyr
305                 310                 315                 320
Glu Leu Gly Lys Glu Phe Leu Pro Met Glu Ala Gln Leu Ser Arg Leu
                325                 330                 335
Ile Gly Gln Ser Leu Trp Asp Val Ser Arg Ser Ser Thr Gly Asn Leu
            340                 345                 350
Val Glu Trp Phe Leu Leu Arg Lys Ala Tyr Glu Arg Asn Glu Leu Ala
        355                 360                 365
Pro Asn Lys Pro Asp Glu Lys Glu Leu Ala Arg Arg Gln Ser Tyr
370                 375                 380
Glu Gly Gly Tyr Val Lys Glu Pro Glu Arg Gly Leu Trp Glu Asn Ile
385                 390                 395                 400
Val Tyr Leu Asp Phe Arg Ser Leu Tyr Pro Ser Ile Ile Ile Thr His
                405                 410                 415
Asn Val Ser Pro Asp Thr Leu Asn Arg Glu Gly Cys Lys Glu Tyr Asp
            420                 425                 430
Val Ala Pro Gln Val Gly His Arg Phe Cys Lys Asp Phe Pro Gly Phe
        435                 440                 445
Ile Pro Ser Leu Leu Gly Asp Leu Leu Glu Glu Arg Gln Lys Ile Lys
450                 455                 460
Lys Lys Met Lys Ala Thr Ile Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Arg Ala Arg Trp Tyr Cys Lys Glu Cys Ala Glu Ser
            500                 505                 510
Val Thr Ala Trp Gly Arg Glu Tyr Ile Thr Met Thr Ile Lys Glu Ile
        515                 520                 525
Glu Glu Lys Tyr Gly Phe Lys Val Ile Tyr Ser Asp Thr Asp Gly Phe
530                 535                 540
Phe Ala Thr Ile Pro Gly Ala Asp Ala Glu Thr Val Lys Lys Lys Ala
545                 550                 555                 560
Met Glu Phe Leu Lys Tyr Ile Asn Ala Lys Leu Pro Gly Ala Leu Glu
                565                 570                 575
Leu Glu Tyr Glu Gly Phe Tyr Lys Arg Gly Phe Phe Val Thr Lys Lys
            580                 585                 590
Lys Tyr Ala Val Ile Asp Glu Glu Gly Lys Ile Thr Thr Arg Gly Leu
        595                 600                 605
```

```
Glu Ile Val Arg Arg Asp Trp Ser Glu Ile Ala Lys Glu Thr Gln Ala
    610                 615                 620
Arg Val Leu Glu Ala Leu Leu Lys Asp Gly Asp Val Lys Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Lys Asp
            660                 665                 670
Tyr Lys Ala Thr Gly Pro His Val Ala Val Ala Lys Arg Leu Ala Ala
        675                 680                 685
Arg Gly Val Lys Ile Arg Pro Gly Thr Val Ile Ser Tyr Ile Val Leu
690                 695                 700
Lys Gly Ser Gly Arg Ile Gly Asp Arg Ala Ile Pro Phe Asp Glu Phe
705                 710                 715                 720
Asp Pro Thr Lys His Lys Tyr Asp Ala Glu Tyr Tyr Ile Glu Asn Gln
                725                 730                 735
Val Leu Pro Ala Val Glu Arg Ile Leu Arg Ala Phe Gly Tyr Arg Lys
            740                 745                 750
Glu Asp Leu Arg Tyr Gln Lys Thr Arg Gln Val Gly Leu Ser Ala Trp
        755                 760                 765
Leu Lys Pro Lys Gly Thr
770

<210> SEQ ID NO 6
<211> LENGTH: 773
<212> TYPE: PRT
<213> ORGANISM: artificial
<220> FEATURE:
<223> OTHER INFORMATION: altered polymerase

<400> SEQUENCE: 6

Met Ile Ile Asp Ala Asp Tyr Ile Thr Glu Asp Gly Lys Pro Ile Ile
1               5                   10                  15
Arg Ile Phe Lys Lys Glu Lys Gly Glu Phe Lys Val Glu Tyr Asp Arg
            20                  25                  30
Thr Phe Arg Pro Tyr Ile Tyr Ala Leu Leu Lys Asp Asp Ser Ala Ile
        35                  40                  45
Asp Glu Val Lys Lys Ile Thr Ala Glu Arg His Gly Lys Ile Val Arg
    50                  55                  60
Ile Thr Glu Val Glu Lys Val Gln Lys Lys Phe Leu Gly Arg Pro Ile
65                  70                  75                  80
Glu Val Trp Lys Leu Tyr Leu Glu His Pro Gln Asp Val Pro Ala Ile
                85                  90                  95
Arg Glu Lys Ile Arg Glu His Pro Ala Val Val Asp Ile Phe Glu Tyr
            100                 105                 110
Asp Ile Pro Phe Ala Lys Arg Tyr Leu Ile Asp Lys Gly Leu Thr Pro
        115                 120                 125
Met Glu Gly Asn Glu Glu Leu Thr Phe Leu Ala Val Asp Ile Glu Thr
    130                 135                 140
Leu Tyr His Glu Gly Glu Glu Phe Gly Lys Gly Pro Ile Ile Met Ile
145                 150                 155                 160
Ser Tyr Ala Asp Glu Glu Gly Ala Lys Val Ile Thr Trp Lys Ser Ile
                165                 170                 175
Asp Leu Pro Tyr Val Glu Val Val Ser Ser Glu Arg Glu Met Ile Lys
            180                 185                 190
```

-continued

Arg Leu Val Lys Val Ile Arg Glu Lys Asp Pro Asp Val Ile Ile Thr
            195                 200                 205

Tyr Asn Gly Asp Asn Phe Asp Phe Pro Tyr Leu Leu Lys Arg Ala Glu
            210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Thr Ile Asn Leu Pro Thr
            260                 265                 270

Tyr Thr Leu Glu Ala Val Tyr Glu Ala Ile Phe Gly Lys Ser Lys Glu
            275                 280                 285

Lys Val Tyr Ala His Glu Ile Ala Glu Ala Trp Glu Thr Gly Lys Gly
            290                 295                 300

Leu Glu Arg Val Ala Lys Tyr Ser Met Glu Asp Ala Lys Val Thr Phe
305                 310                 315                 320

Glu Leu Gly Lys Glu Phe Phe Pro Met Glu Ala Gln Leu Ala Arg Leu
                325                 330                 335

Val Gly Gln Pro Val Trp Asp Val Ser Arg Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
            370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Ile Thr
                405                 410                 415

His Asn Val Ser Pro Asp Thr Leu Asn Arg Glu Asn Cys Lys Glu Tyr
            420                 425                 430

Asp Val Ala Pro Gln Val Gly His Arg Phe Cys Lys Asp Phe Pro Gly
            435                 440                 445

Phe Ile Pro Ser Leu Leu Gly Asn Leu Leu Glu Glu Arg Gln Lys Ile
            450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Gln Tyr Ile Asp Leu Val Arg Arg Glu
            515                 520                 525

Leu Glu Ser Arg Gly Phe Lys Val Leu Tyr Ile Asp Thr Asp Gly Leu
            530                 535                 540

Tyr Ala Thr Ile Pro Gly Ala Lys His Glu Glu Ile Lys Glu Lys Ala
545                 550                 555                 560

Leu Lys Phe Val Glu Tyr Ile Asn Ser Lys Leu Pro Gly Leu Leu Glu
                565                 570                 575

Leu Glu Tyr Glu Gly Phe Tyr Ala Arg Gly Phe Phe Val Thr Lys Lys
            580                 585                 590

Lys Tyr Ala Leu Ile Asp Glu Glu Gly Lys Ile Val Thr Arg Gly Leu
            595                 600                 605

Glu Ile Val Arg Arg Asp Trp Ser Glu Ile Ala Lys Glu Thr Gln Ala
            610                 615                 620

Lys Val Leu Glu Ala Ile Leu Lys His Gly Asn Val Asp Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu Ser Glu
            660                 665                 670

Tyr Lys Ala Ile Gly Pro His Val Ala Val Ala Lys Arg Leu Ala Ala
        675                 680                 685

Lys Gly Val Lys Val Lys Pro Gly Met Val Ile Gly Tyr Ile Val Leu
    690                 695                 700

Arg Gly Asp Gly Pro Ile Ser Lys Arg Ala Ile Ala Ile Glu Glu Phe
705                 710                 715                 720

Asp Pro Lys Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Lys Tyr Gln Lys Thr Lys Gln Val Gly Leu Gly Ala Trp
        755                 760                 765

Leu Lys Phe Gly Ser
    770

<210> SEQ ID NO 7
<211> LENGTH: 775
<212> TYPE: PRT
<213> ORGANISM: artificial
<220> FEATURE:
<223> OTHER INFORMATION: altered polymerase

<400> SEQUENCE: 7

Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asn Tyr Asp Arg
            20                  25                  30

Asp Phe Glu Pro Tyr Ile Tyr Ala Leu Leu Lys Asp Asp Ser Ala Ile
        35                  40                  45

Glu Asp Ile Lys Lys Ile Thr Ala Glu Arg His Gly Thr Thr Val Arg
    50                  55                  60

Val Thr Arg Ala Glu Arg Val Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asn Glu Glu Leu Arg Met Leu Ala Phe Asp Ile Glu Thr
    130                 135                 140

Leu Tyr His Glu Gly Glu Glu Phe Gly Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Glu Ser Val Ser Thr Glu Lys Glu Met Ile Lys
            180                 185                 190

```
Arg Phe Leu Lys Val Ile Gln Glu Lys Asp Pro Asp Val Leu Ile Thr
            195                 200                 205

Tyr Asn Gly Asp Asn Phe Asp Phe Ala Tyr Leu Lys Lys Arg Ser Glu
        210                 215                 220

Thr Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Thr Val Tyr Glu Ala Ile Phe Gly Gln Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Ala Glu Ser Tyr
    370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Thr His
                405                 410                 415

Asn Val Ser Pro Asp Thr Leu Asn Arg Glu Gly Cys Arg Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Asn Ala Arg Trp Tyr Cys Arg Glu Cys Ala Glu Ser
            500                 505                 510

Val Thr Ala Trp Gly Arg Gln Tyr Ile Glu Thr Thr Met Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Thr
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Arg Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605
```

```
Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Arg Tyr Glu Val Pro
                645                 650                 655

Pro Glu Lys Leu Val Ile Tyr Glu Gln Ile Thr Arg Asn Leu Arg Asp
            660                 665                 670

Tyr Arg Ala Thr Gly Pro His Val Ala Val Lys Arg Leu Ala Ala
        675                 680                 685

Arg Gly Ile Lys Ile Arg Pro Gly Thr Val Ile Ser Tyr Ile Val Leu
    690                 695                 700

Lys Gly Pro Gly Arg Val Gly Asp Arg Ala Ile Pro Phe Asp Glu Phe
705                 710                 715                 720

Asp Pro Ala Lys His Arg Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Lys Gln Ala Gly Leu Gly Ala Trp
        755                 760                 765

Leu Lys Pro Lys Thr Gly Ser
770                 775

<210> SEQ ID NO 8
<211> LENGTH: 775
<212> TYPE: PRT
<213> ORGANISM: artificial
<220> FEATURE:
<223> OTHER INFORMATION: altered polymerase

<400> SEQUENCE: 8

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190
```

-continued

```
Arg Phe Leu Arg Val Val Arg Glu Lys Asp Pro Asp Val Leu Ile Thr
            195                 200                 205
Tyr Asn Gly Asp Asn Phe Asp Phe Ala Tyr Leu Lys Lys Arg Ser Glu
            210                 215                 220
Glu Leu Gly Ile Lys Phe Thr Leu Gly Arg Asp Gly Ser Glu Pro Lys
225                 230                 235                 240
Ile Gln Arg Met Gly Asp Tyr Phe Ala Val Glu Val Lys Gly Arg Ile
                    245                 250                 255
His Phe Asp Leu Tyr Pro Val Ile Arg Arg Thr Ile Asn Leu Pro Thr
                260                 265                 270
Tyr Thr Leu Glu Ala Val Tyr Glu Ala Val Phe Gly Lys Pro Lys Glu
                275                 280                 285
Lys Val Tyr Ala Glu Glu Ile Ala Gln Ala Trp Glu Ser Gly Glu Gly
            290                 295                 300
Leu Glu Arg Val Ala Arg Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                    325                 330                 335
Ile Gly Gln Ser Leu Trp Asp Val Ser Arg Ser Ser Thr Gly Asn Leu
                340                 345                 350
Val Glu Trp Phe Leu Leu Arg Lys Ala Tyr Lys Arg Asn Glu Leu Ala
                355                 360                 365
Pro Asn Lys Pro Asp Glu Arg Glu Leu Ala Arg Arg Gly Gly Tyr
            370                 375                 380
Ala Gly Gly Tyr Val Lys Glu Pro Glu Arg Gly Leu Trp Asp Asn Ile
385                 390                 395                 400
Val Tyr Leu Asp Phe Arg Ser Ala Ala Ile Ser Ile Ile Thr His
                    405                 410                 415
Asn Val Ser Pro Asp Thr Leu Asn Arg Glu Gly Cys Lys Glu Tyr Asp
                420                 425                 430
Val Ala Pro Glu Val Gly His Lys Phe Cys Lys Asp Phe Pro Gly Phe
            435                 440                 445
Ile Pro Ser Leu Leu Gly Asp Leu Leu Glu Glu Arg Gln Lys Ile Lys
            450                 455                 460
Arg Lys Met Lys Ala Thr Val Asp Pro Leu Glu Lys Lys Leu Leu Asp
465                 470                 475                 480
Tyr Arg Gln Arg Val Ile Lys Ile Leu Ala Asn Ser Phe Tyr Gly Tyr
                    485                 490                 495
Gly Gly Tyr Ala Lys Ala Arg Trp Tyr Cys Lys Glu Cys Ala Glu Ser
                500                 505                 510
Val Thr Ala Trp Gly Arg Glu Tyr Ile Glu Met Val Ile Arg Glu Leu
                515                 520                 525
Glu Glu Lys Phe Gly Phe Lys Val Leu Tyr Ala Asp Thr Asp Gly Leu
            530                 535                 540
His Ala Thr Ile Pro Gly Ala Asp Ala Glu Thr Val Lys Lys Lys Ala
545                 550                 555                 560
Lys Glu Phe Leu Lys Tyr Ile Asn Pro Lys Leu Pro Gly Leu Leu Glu
                    565                 570                 575
Leu Glu Tyr Glu Gly Phe Tyr Val Arg Gly Phe Phe Val Thr Lys Lys
                580                 585                 590
Lys Tyr Ala Val Ile Asp Asp Glu Gly Lys Ile Thr Thr Arg Gly Leu
                595                 600                 605
```

```
Glu Ile Val Arg Arg Asp Trp Ser Glu Ile Ala Lys Glu Thr Gln Ala
            610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
            770                 775

<210> SEQ ID NO 9
<211> LENGTH: 775
<212> TYPE: PRT
<213> ORGANISM: artificial
<220> FEATURE:
<223> OTHER INFORMATION: altered polymerase

<400> SEQUENCE: 9

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190
```

Arg Phe Leu Arg Val Val Arg Glu Lys Asp Pro Asp Val Leu Ile Thr
    195                 200                 205

Tyr Asn Gly Asp Asn Phe Asp Phe Ala Tyr Leu Lys Lys Arg Ser Glu
210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
                405                 410                 415

Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
                500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
                580                 585                 590

Lys Tyr Ala Val Ile Asp Glu Glu Gly Lys Ile Thr Thr Arg Gly Leu
            595                 600                 605

```
Glu Ile Val Arg Arg Asp Trp Ser Glu Ile Ala Lys Glu Thr Gln Ala
610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
            645                 650                 655

Pro Glu Lys Leu Asp Ile His Glu Gln Ile Thr Arg Asp Leu Arg Asp
        660                 665                 670

Tyr Lys Ala Thr Gly Pro His Val Ala Val Lys Arg Leu Ala Ala
    675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
            725                 730                 735

Val Leu Pro Ala Val Glu Arg Ile Leu Lys Ala Phe Gly Tyr Arg Lys
        740                 745                 750

Glu Asp Leu Arg Tyr Gln Lys Thr Lys Gln Val Gly Leu Gly Ala Trp
    755                 760                 765

Leu Lys Val Lys Gly Lys Lys
770                 775

<210> SEQ ID NO 10
<211> LENGTH: 775
<212> TYPE: PRT
<213> ORGANISM: artificial
<220> FEATURE:
<223> OTHER INFORMATION: altered polymerase

<400> SEQUENCE: 10

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Ser Thr Lys Glu Met Ile Lys
            180                 185                 190
```

```
Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Ser Glu
            210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
            370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
            595                 600                 605
```

```
Glu Ile Val Arg Arg Asp Trp Ser Glu Ile Ala Arg Glu Thr Gln Ala
            610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
                660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
                740                 745                 750

Glu Asp Leu Arg Tyr Gln Lys Thr Lys Gln Val Gly Leu Gly Ala Trp
            755                 760                 765

Leu Lys Val Lys Gly Lys Lys
            770                 775

<210> SEQ ID NO 11
<211> LENGTH: 775
<212> TYPE: PRT
<213> ORGANISM: artificial
<220> FEATURE:
<223> OTHER INFORMATION: altered polymerase

<400> SEQUENCE: 11

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190
```

```
Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
        595                 600                 605
```

```
Glu Ile Val Arg Arg Asp Trp Ser Glu Ile Ala Lys Glu Thr Gln Ala
    610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
770                 775

<210> SEQ ID NO 12
<211> LENGTH: 775
<212> TYPE: PRT
<213> ORGANISM: artificial
<220> FEATURE:
<223> OTHER INFORMATION: altered polymerase

<400> SEQUENCE: 12

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190
```

```
Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Ser Glu
            210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                    245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
            290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                    325                 330                 335

Ile Gly Gln Ser Leu Trp Asp Val Ser Arg Ser Ser Lys Gly Asn Leu
                340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
            370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
                    405                 410                 415

Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                    485                 490                 495

Gly Gly Tyr Ala Lys Ala Arg Trp Tyr Cys Lys Glu Cys Ala Glu Ser
                500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                    565                 570                 575

Leu Glu Tyr Glu Gly Phe Tyr Val Arg Gly Phe Phe Val Thr Lys Lys
                580                 585                 590

Lys Tyr Ala Val Ile Asp Asp Glu Gly Lys Ile Thr Thr Arg Gly Leu
            595                 600                 605
```

-continued

```
Glu Ile Val Arg Arg Asp Trp Ser Glu Ile Ala Lys Glu Thr Gln Ala
    610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
    770                 775

<210> SEQ ID NO 13
<211> LENGTH: 775
<212> TYPE: PRT
<213> ORGANISM: artificial
<220> FEATURE:
<223> OTHER INFORMATION: altered polymerase

<400> SEQUENCE: 13

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
    115                 120                 125

Ala Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190
```

```
Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Phe Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
        595                 600                 605
```

```
Glu Ile Val Arg Arg Asp Trp Ser Glu Ile Ala Lys Glu Thr Gln Ala
    610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
770                 775

<210> SEQ ID NO 14
<211> LENGTH: 775
<212> TYPE: PRT
<213> ORGANISM: artificial
<220> FEATURE:
<223> OTHER INFORMATION: altered polymerase

<400> SEQUENCE: 14

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190
```

```
Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Ser Glu
        210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Ser Gly Lys Pro Lys Glu
        275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
595                 600                 605
```

Glu Ile Val Arg Arg Asp Trp Ser Glu Ile Ala Lys Glu Thr Gln Ala
        610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
                660                 665                 670

Tyr Lys Ala Thr Gly Pro His Val Ala Val Ala Lys Arg Leu Ala Ala
                675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
                740                 745                 750

Glu Asp Leu Arg Tyr Gln Lys Thr Lys Gln Val Gly Leu Gly Ala Trp
                755                 760                 765

Leu Lys Val Lys Gly Lys Lys
            770                 775

<210> SEQ ID NO 15
<211> LENGTH: 775
<212> TYPE: PRT
<213> ORGANISM: artificial
<220> FEATURE:
<223> OTHER INFORMATION: altered polymerase

<400> SEQUENCE: 15

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

```
Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
            370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
        595                 600                 605
```

```
Glu Ile Val Arg Arg Asp Trp Ser Glu Ile Ala Lys Glu Thr Gln Ala
            610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Lys Arg Leu Ala Ala
                675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
                755                 760                 765

Leu Lys Val Lys Gly Lys Lys
770                 775

<210> SEQ ID NO 16
<211> LENGTH: 775
<212> TYPE: PRT
<213> ORGANISM: artificial
<220> FEATURE:
<223> OTHER INFORMATION: altered polymerase

<400> SEQUENCE: 16

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Ser Thr Lys Glu Met Ile Lys
            180                 185                 190
```

```
Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Ser Glu
        210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Asn Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
        595                 600                 605
```

```
Glu Ile Val Arg Arg Asp Trp Ser Glu Ile Ala Lys Glu Thr Gln Ala
            610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
            645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
            725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
            770                 775

<210> SEQ ID NO 17
<211> LENGTH: 775
<212> TYPE: PRT
<213> ORGANISM: artificial
<220> FEATURE:
<223> OTHER INFORMATION: altered polymerase

<400> SEQUENCE: 17

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Ser Thr Glu Lys Glu Met Ile Lys
            180                 185                 190
```

```
Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Cys Asp Asn Ile
385                 390                 395                 400

Val Tyr Leu Asp Phe Arg Ser Ala Ala Ile Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
        595                 600                 605
```

```
Glu Ile Val Arg Arg Asp Trp Ser Glu Ile Ala Lys Glu Thr Gln Ala
    610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
770                 775

<210> SEQ ID NO 18
<211> LENGTH: 775
<212> TYPE: PRT
<213> ORGANISM: artificial
<220> FEATURE:
<223> OTHER INFORMATION: altered polymerase

<400> SEQUENCE: 18

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Ser Thr Lys Glu Met Ile Lys
            180                 185                 190
```

```
Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Ser Glu
            210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
            290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
            370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
            595                 600                 605
```

```
Glu Ile Val Arg Arg Asp Trp Ser Glu Ile Ala Lys Glu Thr Gln Ala
            610                 615                 620

Arg Val Leu Glu Ala Ile Leu Lys Thr Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
            770                 775

<210> SEQ ID NO 19
<211> LENGTH: 775
<212> TYPE: PRT
<213> ORGANISM: artificial
<220> FEATURE:
<223> OTHER INFORMATION: altered polymerase

<400> SEQUENCE: 19

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190
```

```
Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Ser Glu
        210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
        370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Tyr Pro Ala Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
        450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
        530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
        595                 600                 605
```

```
Glu Ile Val Arg Arg Asp Trp Ser Glu Ile Ala Lys Glu Thr Gln Ala
610                 615                 620
Arg Val Leu Glu Ala Ile Leu Lys Gly Gly Asp Val Glu Glu Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Arg Asp
                660                 665                 670
Tyr Lys Ala Thr Gly Pro His Val Ala Val Ala Lys Arg Leu Ala Ala
                675                 680                 685
Arg Gly Val Lys Ile Arg Pro Gly Thr Val Ile Ser Tyr Ile Val Leu
            690                 695                 700
Lys Gly Ser Gly Arg Ile Gly Asp Arg Ala Ile Pro Ala Asp Glu Phe
705                 710                 715                 720
Asp Pro Thr Lys His Arg Tyr Asp Ala Glu Tyr Tyr Ile Glu Asn Gln
                725                 730                 735
Val Leu Pro Ala Val Glu Arg Ile Leu Lys Ala Phe Gly Tyr Arg Lys
                740                 745                 750
Glu Asp Leu Arg Tyr Gln Lys Thr Lys Gln Val Gly Leu Gly Ala Trp
                755                 760                 765
Leu Lys Val Lys Gly Lys Lys
770                 775
```

<210> SEQ ID NO 20
<211> LENGTH: 775
<212> TYPE: PRT
<213> ORGANISM: artificial
<220> FEATURE:
<223> OTHER INFORMATION: altered polymerase

<400> SEQUENCE: 20

```
Met Ile Leu Asp Thr Asp Tyr Ile Thr Glu Asn Gly Lys Pro Val Ile
1               5                   10                  15
Arg Val Phe Lys Lys Glu Asn Gly Glu Phe Lys Ile Glu Tyr Asp Arg
                20                  25                  30
Thr Phe Glu Pro Tyr Phe Tyr Ala Leu Leu Lys Asp Asp Ser Ala Ile
            35                  40                  45
Glu Asp Val Lys Lys Val Thr Ala Lys Arg His Gly Thr Val Val Lys
50                  55                  60
Val Lys Arg Ala Glu Lys Val Gln Lys Lys Phe Leu Gly Arg Pro Ile
65                  70                  75                  80
Glu Val Trp Lys Leu Tyr Phe Asn His Pro Gln Asp Val Pro Ala Ile
                85                  90                  95
Arg Asp Arg Ile Arg Ala His Pro Ala Val Val Asp Ile Tyr Glu Tyr
                100                 105                 110
Asp Ile Pro Phe Ala Lys Arg Tyr Leu Ile Asp Lys Gly Leu Ile Pro
            115                 120                 125
Ala Glu Gly Asp Glu Glu Leu Thr Met Leu Ala Phe Ala Ile Ala Thr
130                 135                 140
Leu Tyr His Glu Gly Glu Glu Phe Gly Thr Gly Pro Ile Leu Met Ile
145                 150                 155                 160
Ser Tyr Ala Asp Gly Ser Glu Ala Arg Val Ile Thr Trp Lys Lys Ile
                165                 170                 175
Asp Leu Pro Tyr Val Asp Val Val Ser Thr Glu Lys Glu Met Ile Lys
                180                 185                 190
```

```
Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Ser Glu
        210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Tyr Pro Ile Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
        595                 600                 605
```

-continued

Glu Ile Val Arg Arg Asp Trp Ser Glu Ile Ala Lys Glu Thr Gln Ala
            610                 615                 620

Arg Val Leu Glu Ala Ile Leu Lys Gly Gly Asp Val Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
                660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
                740                 745                 750

Glu Asp Leu Arg Tyr Gln Lys Thr Lys Gln Val Gly Leu Gly Ala Trp
            755                 760                 765

Leu Lys Val Lys Gly Lys Lys
            770                 775

<210> SEQ ID NO 21
<211> LENGTH: 775
<212> TYPE: PRT
<213> ORGANISM: artificial
<220> FEATURE:
<223> OTHER INFORMATION: altered polymerase

<400> SEQUENCE: 21

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
            115                 120                 125

Ala Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

-continued

```
Arg Phe Leu Arg Val Val Arg Glu Lys Asp Pro Asp Val Leu Ile Thr
            195                 200                 205
Tyr Asn Gly Asp Asn Phe Asp Phe Ala Tyr Leu Lys Lys Arg Ser Glu
            210                 215                 220
Glu Leu Gly Ile Lys Phe Thr Leu Gly Arg Asp Gly Ser Glu Pro Lys
225                 230                 235                 240
Ile Gln Arg Met Gly Asp Tyr Phe Ala Val Glu Val Lys Gly Arg Ile
            245                 250                 255
His Phe Asp Leu Tyr Pro Val Ile Arg Arg Thr Ile Asn Leu Pro Thr
            260                 265                 270
Tyr Thr Leu Glu Ala Val Tyr Glu Ala Val Phe Gly Lys Pro Lys Glu
            275                 280                 285
Lys Val Tyr Ala Glu Glu Ile Ala Gln Ala Trp Glu Ser Gly Glu Gly
            290                 295                 300
Leu Glu Arg Val Ala Arg Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
            325                 330                 335
Ile Gly Gln Ser Leu Trp Asp Val Ser Arg Ser Ser Thr Gly Asn Leu
            340                 345                 350
Val Glu Trp Phe Leu Leu Arg Lys Ala Tyr Lys Arg Asn Glu Leu Ala
            355                 360                 365
Pro Asn Lys Pro Asp Glu Arg Glu Leu Ala Arg Arg Arg Gly Gly Tyr
            370                 375                 380
Ala Gly Gly Tyr Val Lys Glu Pro Glu Arg Gly Leu Trp Asp Asn Ile
385                 390                 395                 400
Val Tyr Leu Asp Phe Arg Ser Tyr Pro Pro Ser Ile Ile Ile Thr His
            405                 410                 415
Asn Val Ser Pro Asp Thr Leu Asn Arg Glu Gly Cys Lys Glu Tyr Asp
            420                 425                 430
Val Ala Pro Glu Val Gly His Lys Phe Cys Lys Asp Phe Pro Gly Phe
            435                 440                 445
Ile Pro Ser Leu Leu Gly Asp Leu Leu Glu Glu Arg Gln Lys Ile Lys
            450                 455                 460
Arg Lys Met Lys Ala Thr Val Asp Pro Leu Glu Lys Lys Leu Leu Asp
465                 470                 475                 480
Tyr Arg Gln Arg Val Ile Lys Ile Leu Ala Asn Ser Phe Tyr Gly Tyr
            485                 490                 495
Gly Gly Tyr Ala Lys Ala Arg Trp Tyr Cys Lys Glu Cys Ala Glu Ser
            500                 505                 510
Val Thr Ala Trp Gly Arg Glu Tyr Ile Glu Met Val Ile Arg Glu Leu
            515                 520                 525
Glu Glu Lys Phe Gly Phe Lys Val Leu Tyr Ala Asp Thr Asp Gly Leu
            530                 535                 540
His Ala Thr Ile Pro Gly Ala Asp Ala Glu Thr Val Lys Lys Lys Ala
545                 550                 555                 560
Lys Glu Phe Leu Lys Tyr Ile Asn Pro Lys Leu Pro Gly Leu Leu Glu
            565                 570                 575
Leu Glu Tyr Glu Gly Phe Tyr Val Arg Gly Phe Phe Val Thr Lys Lys
            580                 585                 590
Lys Tyr Ala Val Ile Asp Asp Glu Gly Lys Ile Thr Thr Arg Gly Leu
            595                 600                 605
```

```
Glu Ile Val Arg Arg Asp Trp Ser Glu Ile Ala Lys Glu Thr Gln Ala
    610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
770                 775
```

<210> SEQ ID NO 22
<211> LENGTH: 775
<212> TYPE: PRT
<213> ORGANISM: artificial
<220> FEATURE:
<223> OTHER INFORMATION: altered polymerase

<400> SEQUENCE: 22

```
Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190
```

```
Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Ser Glu
        210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Lys Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Tyr Pro Ala Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
        595                 600                 605
```

-continued

Glu Ile Val Arg Arg Asp Trp Ser Glu Ile Ala Lys Glu Thr Gln Ala
610                 615                 620

Arg Val Leu Glu Ala Ile Leu Lys Gly Gly Asp Val Glu Ala Val
625                 630                 635                 640

Arg Ile Val Lys Glu Val Thr Glu Lys Leu Ser Lys Tyr Glu Val Pro
            645                 650                 655

Pro Glu Lys Leu Val Ile His Glu Gln Ile Thr Arg Asp Leu Arg Asp
                660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
770                 775

<210> SEQ ID NO 23
<211> LENGTH: 775
<212> TYPE: PRT
<213> ORGANISM: artificial
<220> FEATURE:
<223> OTHER INFORMATION: altered polymerase

<400> SEQUENCE: 23

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

```
Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Ser Glu
        210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Lys Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
        370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Tyr Pro Ile Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
        450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
        595                 600                 605
```

```
Glu Ile Val Arg Arg Asp Trp Ser Glu Ile Ala Lys Glu Thr Gln Ala
            610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
                675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
                755                 760                 765

Leu Lys Val Lys Gly Lys Lys
770                 775

<210> SEQ ID NO 24
<211> LENGTH: 775
<212> TYPE: PRT
<213> ORGANISM: artificial
<220> FEATURE:
<223> OTHER INFORMATION: altered polymerase

<400> SEQUENCE: 24

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190
```

Arg Phe Leu Arg Val Val Arg Glu Lys Asp Pro Asp Val Leu Ile Thr
              195                 200                 205

Tyr Asn Gly Asp Asn Phe Asp Phe Ala Tyr Leu Lys Lys Arg Ser Glu
        210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
        260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Lys Gly Asn Leu
                340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
        370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Tyr Pro Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
595                 600                 605

```
Glu Ile Val Arg Arg Asp Trp Ser Glu Ile Ala Lys Glu Thr Gln Ala
    610             615             620

Arg Val Leu Glu Ala Ile Leu Lys Gly Gly Asp Val Glu Glu Ala Val
625             630             635                         640

Arg Ile Val Lys Glu Val Thr Glu Lys Leu Ser Lys Tyr Glu Val Pro
                645             650                     655

Pro Glu Lys Leu Val Ile His Glu Gln Ile Thr Arg Asp Leu Arg Asp
                660             665             670

Tyr Lys Ala Thr Gly Pro His Val Ala Val Ala Lys Arg Leu Ala Ala
        675             680             685

Arg Gly Val Lys Ile Arg Pro Gly Thr Val Ile Ser Tyr Ile Val Leu
    690             695             700

Lys Gly Ser Gly Arg Ile Gly Asp Arg Ala Ile Pro Ala Asp Glu Phe
705             710             715                     720

Asp Pro Thr Lys His Arg Tyr Asp Ala Glu Tyr Tyr Ile Glu Asn Gln
                725             730             735

Val Leu Pro Ala Val Glu Arg Ile Leu Lys Ala Phe Gly Tyr Arg Lys
            740             745             750

Glu Asp Leu Arg Tyr Gln Lys Thr Lys Gln Val Gly Leu Gly Ala Trp
        755             760             765

Leu Lys Val Lys Gly Lys Lys
    770             775
```